US008993625B2

(12) United States Patent
Driscoll

(10) Patent No.: US 8,993,625 B2
(45) Date of Patent: Mar. 31, 2015

(54) METHOD OF MITIGATING ADVERSE DRUG EVENTS USING OMEGA-3 FATTY ACIDS AS A PARENTERAL THERAPEUTIC DRUG VEHICLE

(75) Inventor: David F. Driscoll, Bridgewater, MA (US)

(73) Assignee: Stable Solutions LLC, Goleta, CA (US)

(*) Notice: Subject to any disclaimer, the term of this patent is extended or adjusted under 35 U.S.C. 154(b) by 367 days.

(21) Appl. No.: 13/230,316

(22) Filed: Sep. 12, 2011

(65) Prior Publication Data

US 2012/0022001 A1 Jan. 26, 2012

Related U.S. Application Data

(63) Continuation-in-part of application No. 12/923,257, filed on Sep. 10, 2010, now abandoned, which is a continuation-in-part of application No. 12/382,196, filed on Mar. 11, 2009, now Pat. No. 8,241,672, and a continuation-in-part of application No. PCT/US2010/000723, filed on Mar. 11, 2010, which is a continuation-in-part of application No. 12/382,196, filed on Mar. 11, 2009, now Pat. No. 8,241,672.

(51) Int. Cl.

| | |
|---|---|
| A01N 37/00 | (2006.01) |
| A61K 31/20 | (2006.01) |
| A61K 35/60 | (2006.01) |
| A61K 38/13 | (2006.01) |
| A01N 37/18 | (2006.01) |
| A61K 31/65 | (2006.01) |
| A01N 43/38 | (2006.01) |
| A61K 31/40 | (2006.01) |
| A61K 31/202 | (2006.01) |
| A61K 31/436 | (2006.01) |
| A61K 31/232 | (2006.01) |
| A61K 31/343 | (2006.01) |
| A61K 31/405 | (2006.01) |
| A61K 31/407 | (2006.01) |
| A61K 31/47 | (2006.01) |
| A61K 31/52 | (2006.01) |
| A61K 31/616 | (2006.01) |
| A61K 31/7036 | (2006.01) |
| A61K 31/7048 | (2006.01) |
| A61K 9/00 | (2006.01) |
| A61K 47/14 | (2006.01) |
| A61K 9/107 | (2006.01) |
| A61K 45/06 | (2006.01) |

(52) U.S. Cl.

CPC .............. *A61K 31/202* (2013.01); *A61K 38/13* (2013.01); *A61K 31/436* (2013.01); *A61K 31/232* (2013.01); *A61K 31/343* (2013.01); *A61K 31/405* (2013.01); *A61K 31/407* (2013.01); *A61K 31/47* (2013.01); *A61K 31/52* (2013.01); *A61K 31/616* (2013.01); *A61K 31/65* (2013.01); *A61K 31/7036* (2013.01); *A61K 31/7048* (2013.01); *A61K 9/0019* (2013.01); *A61K 47/14* (2013.01); *A61K 9/107* (2013.01); *A61K 45/06* (2013.01); *A61K 35/60* (2013.01)

USPC .......... 514/558; 424/523; 514/20.5; 514/154; 514/413

(58) Field of Classification Search

CPC ............ A61K 2300/00; A61K 9/0019; A61K 31/7048; A61K 9/1075; A61K 47/24; A61K 31/202; A61K 31/232; A61K 31/343; A61K 31/405; A61K 31/407; A61K 31/436; A61K 31/47; A61K 31/52; A61K 31/616; A61K 31/65; A61K 31/7036; A61K 35/60; A61K 35/612; A61K 38/13; A61K 47/14; A61K 47/44; A61K 9/107; A61K 31/683; A61K 47/10; A61K 47/20; A61K 47/46; A61K 31/20; A61K 31/216; A61K 31/355; A61K 45/06; A61K 47/12; G01N 33/03

See application file for complete search history.

(56) References Cited

U.S. PATENT DOCUMENTS

| | | | |
|---|---|---|---|
| 5,118,493 A | 6/1992 | Kelley et al. | |
| 5,278,149 A | 1/1994 | Provost et al. | |
| 5,574,065 A | 11/1996 | Trimbo | |
| 5,650,172 A | 7/1997 | Matsuda et al. | |
| 5,698,594 A | 12/1997 | Breivik et al. | |
| 5,739,152 A | 4/1998 | Andersson et al. | |
| 5,780,451 A | 7/1998 | DeMichele et al. | |
| 5,874,470 A | 2/1999 | Nehne et al. | |
| 5,886,037 A | 3/1999 | Klor et al. | |
| 6,008,248 A | 12/1999 | Pscherer et al. | |
| 6,020,020 A | 2/2000 | Cain et al. | |

(Continued)

FOREIGN PATENT DOCUMENTS

| | | |
|---|---|---|
| DE | 196 48 566 A1 | 6/1997 |
| EP | 0 687 418 A2 | 12/1995 |

(Continued)

OTHER PUBLICATIONS

Omegaven package insert.*
Omegaven Package Insert, Oct. 1, 2002.*
Yvon Carpentier et al., "Rapid Cellular Enrichment of Eicosapentaenoate After a Single Intravenous Injection of a Novel Medium-Chain Triacylglycerol:Fish-Oil Emulsion in Humans," *American Journal of Clinical Nutrition*, Feb. 10, 2010, pp. 1-8, doi: 10.3945/ajcn.2009.27951, American Society for Nutrition, Bethesda, Maryland, USA.

(Continued)

*Primary Examiner* — Chris R Tate
*Assistant Examiner* — Douglas F White
(74) *Attorney, Agent, or Firm* — Buchanan Ingersoll & Rooney PC

(57) ABSTRACT

A method of parenterally administering a composition, the method including parenterally administering to a person a composition including at least one omega-3 fatty acid and at least one drug, wherein the at least one omega-3 fatty acid source and the at least one drug are administered simultaneously.

40 Claims, 13 Drawing Sheets

(56) References Cited

U.S. PATENT DOCUMENTS

| | | | |
|---|---|---|---|
| 6,159,523 A | 12/2000 | Cain et al. | |
| 6,284,268 B1 | 9/2001 | Mishra et al. | |
| 6,319,243 B1 | 11/2001 | Becker et al. | |
| 6,417,233 B1 | 7/2002 | Sears et al. | |
| 6,432,439 B1 | 8/2002 | Suzuki et al. | |
| 6,569,853 B1* | 5/2003 | Borisy et al. | 514/226.2 |
| 7,150,996 B2 | 12/2006 | Nicoli et al. | |
| 7,323,206 B1 | 1/2008 | Driscoll et al. | |
| 7,560,486 B2 | 7/2009 | Carpentier et al. | |
| 2002/0107265 A1 | 8/2002 | Chen et al. | |
| 2003/0068385 A1* | 4/2003 | Moyer et al. | 424/523 |
| 2003/0144356 A1 | 7/2003 | Goodale | |
| 2004/0053993 A1* | 3/2004 | Constantinides et al. | 514/458 |
| 2004/0077724 A1 | 4/2004 | Remmereit et al. | |
| 2004/0142040 A1 | 7/2004 | Dong et al. | |
| 2004/0247693 A1 | 12/2004 | Carpentier et al. | |
| 2005/0027004 A1 | 2/2005 | Kyle et al. | |
| 2005/0282840 A1* | 12/2005 | Ross et al. | 514/269 |
| 2006/0067952 A1* | 3/2006 | Chen | 424/400 |
| 2006/0127491 A1 | 6/2006 | Puder et al. | |
| 2006/0211762 A1 | 9/2006 | Rongen et al. | |
| 2007/0071777 A1 | 3/2007 | Bromer et al. | |
| 2007/0148259 A1 | 6/2007 | Gupta | |

FOREIGN PATENT DOCUMENTS

| | | |
|---|---|---|
| EP | 0 780 124 A1 | 6/1997 |
| EP | 1 279 400 A1 | 1/2003 |
| EP | 1 408 931 B1 | 3/2009 |
| WO | WO 90/08544 A1 | 8/1990 |
| WO | WO 97/19683 A1 | 6/1997 |
| WO | 0149284 A1 | 7/2001 |
| WO | 0189474 A2 | 11/2001 |
| WO | WO 03/009828 A1 | 2/2003 |
| WO | 2008036353 A2 | 3/2008 |
| WO | 2010104575 A2 | 9/2010 |

OTHER PUBLICATIONS

Notification of Transmittal of the International Search Report and the Written Opinion of the International Searching Authority, or the Declaration (Form PCT/ISA/220), International Search Report (Form PCT/ISA/210), and Written Opinion of the International Searching Authority (Form PCT/ISA/237), dated Jan. 6, 2011, issued in corresponding International Application No. PCT/US2010/000723.

Abulrob et al., *The effect of fatty acids and analogues upon intracellular levels of doxorubicin in cells displaying P-glycoprotein mediated multidrug resistance*, 8(4) J Drug Target 247-256 (2000) (abstract only).

Calviello et al., *Docosahexaenoic acid enhances the susceptibility of human colorectal cancer cells to 5-fluorouracil*, 55(1) Cancer Chemother Pharmacol Jan. 12-20, 2005 (abstract only).

Elzinga et al., *Modification of experimental nephrotoxicity with fish oil as the vehicle for cyclosporine*, 43(2) Transplantation 271-274 (Feb. 1987) (abstract only).

Fracasso et al., *Phase 1 and pharmacokinetic study of weekly docosahexaenoic acid-paclitaxel, Taxoprexin, in resistant solid tumor malignancies*, 63(3) Cancer Chemother Pharmacol 451-458 (Feb. 2009) (abstract only).

Futamura, *Toxicity of amiodarone on mouse pulmonary endothelial cells cultured with or without alveolar macrophages*, 21(4) J Toxicol Sci 253-267 (Nov. 1996) (abstract only).

Germain et al., *Anthracycline-induced cardiac toxicity is not increased by dietary omega-3 fatty acids*, 47(2) Pharmacol Res 111-117 (Feb. 2003) (abstract only).

Heller et al., *Omega-3 fatty acids improve the diagnosis-related clinical outcome*, 34(4) Crit Care Med 972-979 (Apr. 2006) (abstract only).

Julien et al., *Postmortem brain fatty acid profile of levodopa-treated Parkinson disease patients and parkinsonian monkeys*, 48(5) Neurochem Int, 404-414 (Apr. 2006) (abstract only).

Mahéo et al., *Differential sensitization of cancer cells to doxorubicin by DHA: a role for lipoperoxidation*, 39(6) Free Radic Biol Med 742-751 (Sep. 2005) (abstract only).

Menendez et al., *Exogenous supplementation with omega-3 polyunsaturated fatty acid docosahexaenoic acid (DHA; 22:6n-3) synergistically enhances taxane cytotoxicity and downregulates Her-2/neu (c-erbB-2) oncogene expression in human breast cancer cells*, 14(3) EuR J Cancer Prey 263-270 (Jun. 2005) (abstract only).

Priyamvada et al., *Studies on the protective effect of dietary fish oil on gentamicin-induced nephrotoxicity and oxidative damage in rat kidney*, 78(6) Prostaglandins Leukot Essent Fatty Acids 369-381 (Jun. 2008) (abstract only).

Rudra et al., *Cell-specific enhancement of doxorubicin toxicity in human tumour cells by docosahexaenoic acid*, 21(1A) Anticancer Res 29-38 (Jan.-Feb. 2001) (abstract only).

Wang et al., *Synthesis and preliminary antitumor activity evaluation of a DHA and doxorubicin conjugate*, 16(11) Bioorg Med Chem Lett 2974-2977 (Jun. 1, 2006) (abstract only).

Wichmann et al., *Evaluation of clinical safety and beneficial effects of a fish oil containing lipid emulsion (Lipoplus, MLF541): data from a prospective, randomized, multicenter trial*, 35(3) Crit Care Med 700-706 (Mar. 2007) (abstract only).

Yang et al., *Attenuation of ciclosporin-induced nephrotoxicity by dietary supplementation of seal oil in Sprague-Dawley rats*, 57(11) J Pharm Pharmacol 1485-1492 (Nov. 2005) (abstract only).

Bougnoux et al., *Improving outcome of chemotherapy of metastatic breast cancer by docosahexaenoic acid: a phase II trial*, 101(12) BR J Cancer 1978-1985 (Dec. 15, 2009).

Colas et al., *Sensitization by dietary docosahexaenoic acid of rat mammary carcinoma to anthracycline: a role for tumor vascularization*, 12(19) Clin Cancer Res 5879-5886 (Oct. 1, 2006).

Ding et al., *Differential sensitivity of cancer cells to docosahexaenoic acid-induced cytotoxicity: the potential importance of down-regulation of superoxide dismutase 1 expression*, 3(9) Mol Cancer Ther 1109-1117 (Sep. 2004).

Gonzalez-Periz et al., *Docosahexaenoic acid (DHA) blunts liver injury by conversion to protective lipid mediators: protectin D1 and 17S-hydroxy-DHA*, 20(14) FASEB J 2537-2539, E1844-E1855 (Dec. 2006).

Harries et al., *Phase I/II study of DHA-paclitaxel in combination with carboplatin in patients with advanced malignant solid tumours*, 91(9) Br J Cancer 1651-1655 (Nov. 1, 2004).

Manni et al., *The impact of fish oil on the chemopreventive efficacy of tamoxifen against development of N-methyl-N-nitrosourea-induced rat mammary carcinogenesis*, 3(3) Cancer Prey Res (PHILA PA) 322-330 (Mar. 2010).

Matta et al., *TRPV1 is a novel target for omega-3 polyunsaturated fatty acids*, 578(Pt 2) J Physiol 397-411 (Jan. 15, 2007).

Driscoll, U.S. Appl. No. 12/382,196, entitled "Omega-3 enriched fish oil-in-water parenteral nutrition emulsions", filed in the U. S. Patent and Trademark Office on Mar. 11, 2009.

Driscoll, U.S. Appl. No. 13/255,828, entitled, "Omega-3 Enriched Fish Oil-In-Water Parenteral Nutrition Emulsions", filed in the U. S. Patent and Trademark Office Nov. 1, 2011.

Driscoll, U.S. Appl. No. 12/923,257, entitled, "Method of Mitigating Adverse Drug Events Using Omega-3 Fatty Acids As a Parenteral Therapeutic Drug Vehicle", filed in the U. S. Patent and Trademark Office Sep. 10, 2010.

Official Action issued in Driscoll, U.S. Appl. No. 12/382,196, Nov. 4, 2011, U. S. Patent and Trademark Office (14 pages).

Extended Search Report issued by the European Patent Office issued in corresponding European Patent Application No. 10751124.8 dated Feb. 1, 2012 (5 pages).

Driscoll, David F., "Lipid Injectable Emulsions: Pharmacopeial and Safety Issues," *Pharmaceutical Research*, Sep. 2006, pp. 1959-1969, vol. 23, No. 9, Springer Science + Business Media, Inc., NY, USA.

Driscoll, David F., Letter to the Editor, *Journal of Parenteral and Enteral Nutrition*, Jul./Aug. 2009, pp. 451-452, vol. 33, No. 4, The American Society for Parenteral & Enteral Nutrition, http://pen.sagepub.com.

Lowell, J.A., et al., "Postoperative fluid overload: not a benign problem," *Crit Care Med*, Jul. 1990;18(7):728-733, PubMed (Abstract only).

(56) References Cited

OTHER PUBLICATIONS

Mathru, Mali, et al., "Effect of Fast vs Slow Intralipid Infusion on Gas Exchange, Pulmonary Hemodynamics, and Prostaglandin Metabolism," *Clinical Investigations in Critical Care, Chest*, Feb. 1991, pp. 426-429, 99, American College of Chest Physicians, USA.

Prasertsom, W., et al., "Pulmonary vascular resistance during lipid infusion in neonates," *Arch Dis Child*, 1996;74:F95-98, Children's Health Centre and Perinatal Research Centre, University of Alberta, CA.

Ling, P.R., et al., "Inflammatory mediators in patients receiving long-term home parenteral nutrition," *Digestive Disease Science*, Nov. 2001;46(11):2484-9, PubMed (Abstract only).

Driscoll, David F., et al., "The influence of medium-chain triglycerides on the stability of all-in-one formulations," *International Journal of Pharmaceutics*, 2002, pp. 1-10, 240, Elsevier Science B.V., The Netherlands.

Bistrian, Bruce R., "Clinical Aspects of Essential Fatty Acid Metabolism; Jonathan Rhoads Lecture," *Journal of Parenteral and Enteral Nutrition*, 2003, pp. 168-175, vol. 27, No. 3, Sage, The American Society for Parenteral & Enteral Nutrition, http://pen.sagepub.com/content/27/3/168

Gura, K.M., et al., "Use of a fish oil-based lipid emulsion to treat essential fatty acid deficiency in a soy allergic patient receiving parenteral nutrition," *Clinical Nutrition*, Oct. 2005;24(5):839-47, PubMed (Abstract only).

Wales, P.W., et al., "Neonatal short bowel syndrome: a cohort study," *Journal of Pediatric Surgery*, May 2005;40(5):755-62, PubMed (Abstract only).

Paquot, N., et al., "Fatty liver in the intensive carenit," *Curr Opin Clin Nutr Metab Care*, Mar. 2005;8(2):183-87, PubMed (Abstract only)

Lee, J.S., et al., "Saturated, but not n-6 polyunsaturated, fatty acids induce insulin resistance: role of intramuscular accumulation of lipid metabolites," *J Appl Phvsiol*, May 2006;100(5):1467-74, PubMed (Abstract only).

Gura, Kathleen M., et al., "Reversal of Parenteral Nutrition-Associated Liver Disease in Two Infants With Short Bowel Syndrome Using Parenteral Fish Oil: Implications for Future Management," *Pediatrics*, Jul. 2006, pp. e197-e201, vol. 118, No. 1, American Academy of Pediatrics, USA.

Stanley, J.C., et al., "UK Food Standards Agency Workshop Report: the effects of the dietary n-6: n-3 fatty acid ratio on cardiovascular health," *British Journal of Nutrition*, Dec. 2007; 98(6):1305-1310, PubMed (Abstract only).

Wanten, Geert JA, et al., "Immune modulation by parenteral lipid emulsions [1,2]," *American Journal of Clinical Nutrition* 2007, pp. 1171-1184, 85, American Society for Nutrition, USA.

Driscoll, David F., et al., "Pharmacopeial compliance of fish oil-containing parenteral lipid emulsion mixtures: Globule size distribution (GSD) and fatty acid analyses," *International Journal of Pharmaceutics*, 2009, pp. 125-130, vol. 379, Elsevier B.V., The Netherlands.

Wang, Xinying, et al.,"w -3 Fatty Acids—Supplemented Parenteral Nutrition Decreases Hyperinflammatory Response and Attenuates Systemic Disease Sequelae in Severe Acute Pancreatitis: A Randomized and Controlled Study," *Journal of Parenteral and Enteral Nutrition*, May/Jun. 2008, pp. 236-241, vol. 32, No. 3, Sage, The American Society for Parenteral & Enteral Nutrition, http://pen.sagepub.com/content/32/3/236.

Simoens, Christina M., et al., "Inclusion of 10% fish oil in mixed medium-chain triacylglycerol-long-chain triacylglycerol emulsions increases plasma triacylglycerol clearance and induces rapid eicosapentaenoic acid (20:5n-3) incorporation into blood cell phospholipids [1-3]," *American Journal of Clinical Nutrition*, 2008, pp. 282-288, vol. 88, American Society for Nutrition, USA.

"Globule Size Distribution in Lipid Injectable Emulsions," United States Pharmacopoeia 32, Chapter <729>, 2009, pp. 283-285, Physical Tests.

"Fish Oil, Rich in Omega-3 Acids, Piscis Oleum Omega-3 Acidis Abundans," *European Pharmacopoeia 6.0*, Jan. 2008:1912, 2008, pp. 1893-1895, Monograph 1912.

"Omega-3-Acid Triglycerides: Omega-3 Acidorum Triglycerida," *European Pharmacopoeia 5.4*, Jan. 2005:1352 corrected, 2005, pp. 3995-3997, Monograph 1352.

"Triglycerides, Medium-Chain, Triglycerida Saturata Media," *European Pharmacopoeia 6.0*, Jan. 2008:0868, 2007, pp. 3122-3124, Monograph 0868.

Friesecke, S., et al., "Fish oil supplementation in the parenteral nutrition of critically ill medical patients: a randomised controlled trial," *Intensive Care Med*, Aug. 2008;34(8)1411-20, Epub Mar. 21, 2008, PubMed (Abstract only).

Calder, P.C., "Rationale and use of n-3 fatty acids in artificial nutrition", *Proc Nutr Soc*, Nov. 2010;69(4):565-73, Epub May 5, 2010, Erratum in Proc Nutr Soc, May 2011;70(2):282, PubMed (Abstract only).

"PrestoBlue ™ Cell Viability Reagent", Life Technologies, http://www.invitrogen.com/site/us/en/home/brands/Molecular-Probes/Key-Molecular-Probes-Products/PrestoBlue-Cell-Viability-Reagent.html, 2012, Life Technologies Corporation.

Mansour, N R., et al., "Comparison of microscopy and alamar blue reduction in a larval based assay for schistosome drug screening," *PloS Negl Trop Dis*, Aug. 2010, 4(8):e795, PubMed (Abstract only).

Nociari, M.M., et al., "A novel one-step, highly sensitive fluorometric assay to evaluate cell-mediated cytotoxicity," *J Immunol Methods*, Apr. 1998, 213(2):157-67, PubMed (Abstract only).

Hamid, R., et al., "Comparison of alamar blue and MTT assays for high through-put screening," *Toxicol In Vitro*, Oct. 2004, 18(5):703-10, PubMed (Abstract only).

Van Der Harst, M.R., et al., "Gentamicin Nephrotoxicity—A Comparison of In Vitro Findings with In Vivo Experiments in Equines," *Veterinary Research Communications*, 2005, 29(3), pp. 247-261, Springer.

Al-Nasiry, S., et al., "The use of Alamar Blue assay for quantitative analysis of viability, migration and invasion of choriocarcinoma cells,"*Human Reproduction*, May 2007, 22(5):1304-09, Epub Feb. 16, 2007, PubMed (Abstract only).

Sykes, M.L., et al., "Development of an Alamar Blue ™ Viability Assay in 384-Well Format for High Throughput Whole Cell Screening of *Trypanosoma brucei brucei* Bloodstream Form Strain 427," *Am J Trop Med Hyg*, 2009, 81(4), pp. 665-74, The American Society of Tropical Medicine and Hygiene, USA.

Calder, P.C., et al., "The 2008 ESPEN David Cuthbertson Lecture: Fatty acids and inflammation—from the membrane to the nucleus and from the laboratory bench to the clinic," *Clin Nutr*, Feb. 2010, 29(1):5-12, PubMed (Abstract only).

International Search Report issued in Application No. PCT/US2011/001567 mailed Dec. 2, 2011.

\* cited by examiner

METHOD OF MITIGATING ADVERSE DRUG EVENTS USING OMEGA-3 FATTY ACIDS AS A PARENTERAL THERAPEUTIC DRUG VEHICLE

CROSS-REFERENCE TO RELATED APPLICATIONS

This application claims the benefit of priority and is a continuation-in-part of U.S. application Ser. No. 12/923,257 filed on Sep. 10, 2010, the entire contents of which are incorporated by reference. U.S. application Ser. No. 12/923,257 claims the benefit of priority and is a continuation-in-part of U.S. application Ser. No. 12/382,196 filed on Mar. 11, 2009, and is a continuation-in-part of International Application No. PCT/US2010/000723 filed on Mar. 11, 2010, which in turn is a continuation-in-part of U.S. application Ser. No. 12/382, 196 filed on Mar. 11, 2009, the entire contents of both of which are incorporated by reference herein.

BACKGROUND

1. Field

The present disclosure relates to medicinal formulations that can, for example, contain sufficient amounts of parenteral omega-3 fatty acids derived from naturally-occurring marine oils, and that can function as a novel "therapeutic" drug carrier, or vehicle. This proposed novel application is in contrast to conventional "pharmaceutical" drug carriers, or vehicles.

The marine oil-containing formulations can be in the form of an emulsion drug vehicle, comprising omega-3 fatty acids, attached to triglyceride or ester molecules, as an oil component of the emulsion, in addition to a water component. These two components of the emulsion, with the aid of a suitable surfactant, can exist as separate, but miscible phases, along with one or more drugs that, when parenterally administered without accompanying omega-3 fatty acids-containing marine oil, would often be expected to cause collateral damage to a vital organ. The novel marine oil-containing formulation can be given by intravenous administration, as an oil-in-water emulsion containing the drug(s). The addition of the omega-3 fatty acids (for example, eicosapentaenoic acid (EPA), docosahexaenoic acid (DHA) and/or docosapentaenoic acid (DPA)) to formulations containing selected drugs can reduce at least one adverse event profile of those drugs upon intravenous administration. The at least one adverse event profile can result from a drug toxicity, and can be manifested by oxidative stress, inflammation, immune stimulation or ischemia of one or more vital organs, or a combination thereof.

2. Related Art

Bioactive omega-3, or n3, fatty acids (n3-FAs) are present in naturally-occurring marine oil triglycerides and are contained in a variety of commercial products as nutritional supplements, in such forms, for example, as soft gelatin capsules, foods, enteral nutrition formulations, and parenteral oil-in-water nutrition emulsions. As well, semi-synthetically-derived n3-FAs also exist in a highly purified form, such as omega-3 acid ethyl esters in liquid-filled capsules, used for the treatment of hypertriglyceridemia. The bioactive components of marine oils can consist of three main omega-3 fatty acids: namely, eicosapentaenoic acid (EPA), docosahexaenoic acid (DHA) and, to a lesser extent, docosapentaenoic acid (DPA).

In the critical care setting, the administration of clinical nutrition supplemented with omega-3 fatty acids in fish oil-containing lipid injectable emulsions has been shown to reduce mortality, the use of antibiotics and the length of hospital stay (Reference [8] and [17]). These general beneficial effects were observed in acutely ill surgical patients, but the specific reasons for these positive findings were not clear, as noted by the following excerpt from one of the study conclusions: "In view of the lack of substantial study literature concerning diagnosis-related nutritional single-substrate intervention in the critically ill, the present data can be used in formulating hypotheses . . . ." (Reference [8]). In other words, there is evidence to support the general, or nonspecific, clinical benefits of providing n3-FAs to acutely ill patients, but the reasons for these benefits are poorly understood.

By comparison, in critically ill medical patients, supplementation with fish oil parenteral nutrition emulsions did not affect inflammation or outcome (Reference [33]). Finally, in a recent review about the role of fish oil-containing parenteral nutrition emulsions, the following statement summarizes their present status in clinical medicine: " . . . the influence on inflammatory processes, immune function and clinical endpoints is not clear, since there are too few studies and those that are available report contradictory findings" (Reference [31]). Due to the heterogeneity of patient populations, and the complex array of diseases and treatments, present application of n3-FAs as such, is non-specific. Moreover, there are significant qualitative differences with respect to available fish oil emulsions and various oil compositions (U.S. application Ser. No. 12/382,196 and International Application No. PCT/US2010/000723), further masking any potential clinical benefits.

SUMMARY

A embodiment of the present invention is a pharmaceutical composition for parenteral administration comprising at least one omega-3 fatty acid and at least one drug.

A further embodiment is a pharmaceutical composition for parenteral administration comprising a) an omega-3-fatty acid component selected from the group consisting of omega-3-fatty acid triglycerides and/or omega-3-fatty acid ester, such as omega-3 fatty acid ethyl ester; and b) at least one drug.

Preferably, the parenteral administration of the composition of the invention is an intravenous administration.

An exemplary embodiment can address a significant aspect in the treatment of acutely ill patients requiring intravenous support, namely drug therapy, which can be a significant contributor to determining clinical outcome. Intravenous therapies can be prescribed in various settings (for example, hospital, ambulatory care, hospice, nursing home, rehabilitation or home) depending upon the patient, the disease and the prognosis. The co-administration of a parenteral drug known to cause damage to vital organs, but now accompanied by specific n3-FAs as a therapeutic drug vehicle, at the onset of medication therapy, can allow rapid incorporation of n3-FAs into plasma cell membranes. The n3-FAs can replace n6-FAs present from typical dietary sources, and therefore the former can reduce injury to these vital organs, for example, by altering the production of lipid mediators produced, and, likely improving clinical outcomes.

According to an exemplary aspect, a method of parenterally administering a composition is provided, the method comprising parenterally administering to a person a composition comprising at least one omega-3 fatty acid and at least one drug, wherein the at least one omega-3 fatty acid and the at least one drug are administered simultaneously.

Therefore, according to a preferred embodiment of the pharmaceutical composition the at least one omega-3 fatty acid and the at least one drug are administered simultaneously. In one embodiment of the present invention the pharmaceutical composition can also be consisting of a pharmaceutical system wherein the individual components of the composition are partly or completely separated from each other. The pharmaceutical system can have two or more compartments. A further embodiment of the invention is a pharmaceutical system for parenteral administration comprising at least two compartments a) the first compartment comprising an omega-3-fatty acid component selected from the group consisting of omega-3-fatty acid triglycerides and omega-3-fatty acid ester, such as omega-3 fatty acid ethyl ester; and b) the second compartment comprising at least one drug, wherein said omega-3-fatty acid component and said drug are administered simultaneously. In an exemplary embodiment prior to the administration of the components present in the compartments of the pharmaceutical system a mixing step is conducted wherein the content of the first compartment is combined with the content of the second compartment. Alternatively, the content of the first container and the content of the second container can be administered to the patient individually but simultaneously. According to a preferred embodiment the content of the first compartment is administered intravenously while at the same time the content of the second compartment is administered, preferably administered intravenously. Preferably, the first compartment comprises the omega-3-fatty acid component as a oil in water emulsion and the second compartment comprises a drug dissolved in a liquid, preferably water. For hospitals and in case of emergencies a kit comprising the different components of the pharmaceutical composition of the invention can be helpful. A further embodiment of the present invention is a kit comprising a) one or more sterile container(s) comprising an omega-3-fatty acid component selected from the group consisting of omega-3-fatty acid triglycerides and omega-3-fatty acid ester, such as omega-3 fatty acid ethyl ester; and b) one or more sterile container(s) comprising at least one drug.

Prior to the administration to the patient the content of the different sterile containers of the kit of the invention can be mixed to form the pharmaceutical composition of the invention. Alternatively, the content of the different sterile container(s) can be administered to the patient separately but simultaneously.

According to an exemplary aspect, a composition can contain bioavailable amounts of naturally- or synthetically-derived omega-3 fatty acids (i.e., n3-fatty acids, or n3-FAs). The omega-3 fatty acids can be present in a sufficient concentration as a pharmaceutical product in order to provide a therapeutic benefit, along with a prescribed drug whose side effect profile is associated with significant damage to vital organs. This combination can form a unique "therapeutic drug vehicle", or "TDV" (U.S. application Ser. No. 12/382,196 and International Application No. PCT/US2010/000723).

According to another exemplary aspect, a composition containing both at least one prescribed drug and n3-FA-containing oil, as an oil-containing injectable emulsion, is administered by an intravenous route of administration.

According to another exemplary aspect, a combined intravenous administration of concentrated n3-FAs and at least one prescribed drug known to cause collateral damage to vital organs in a single injectable formulation can ensure the highest bioavailability and rapid incorporation of n3-FAs into plasma membranes not achievable by the oral or enteral routes of administration.

According to another exemplary aspect, at least one adverse consequence of drug toxicity to vital organs can be ameliorated or eliminated by the pharmacological actions of the n3-FAs, EPA, DHA and/or DPA, which can act to reduce organ injury from pronounced oxidative stress, inflammation, immune modulation, and/or ischemia affecting one or more vital organs.

According to another exemplary aspect, amounts of bioactive n3-FAs, i.e., the sum of EPA, DHA and/or DPA, ranging in total concentration from 1 to 300 mg/kg, are present in a parenteral formulation in order to mitigate damage to one or more vital organs caused by the at least one prescribed drug that is/are also present in the composition.

According to another exemplary aspect, the type(s) and relative amounts of bioactive n3-FAs present in the formulation can vary from 0 to 100% for each n3-FA oil component, for example, EPA, DHA and DPA, for a given total concentration of all n3-FA oil components.

According to another exemplary aspect, the effective combination (EPA±DHA±DPA) and dose of n3-FAs (1 mg/kg to 300 mg/kg), along with each prescribed drug in the injectable formulation can be n3FA+drug-specific, n3-FA+drug category-specific, or apply to a broad spectrum of drugs that respond to a specific combination-dose n3-FA regimen.

According to another exemplary aspect, the prescribed drug can reside in either the oil fraction or the water fraction of the injectable formulation, i.e., within the "dispersed" (i.e., "internal") or "continuous" (i.e., "external") phase of an emulsion, depending on whether the drug is oil-soluble or water-soluble, respectively. Accordingly, the lack of pharmaceutical consequence of the location of the drug, i.e., whether it resides in the dispersed or continuous phase, is novel in this disclosure. That is, the drug in most traditional drug-based injectable emulsions is usually water-insoluble, and therefore it necessarily almost always resides in the dispersed (oil) phase. Consequently, such emulsions primarily serve only as drug carriers, or pharmaceutical drug vehicles. In contrast, in the present disclosure, the n3-FA oil-containing "carrier" itself can play an active pharmacological role as a therapeutic drug vehicle, independent of whether the drug resides in the oil or water fraction of the emulsion, for example, regardless of whether it is located in the internal (dispersed) or external (continuous) phase of the emulsion.

According to another exemplary aspect, the n3-FAs combined with a particular drug can accentuate the pharmacological actions of the intended drug therapy, independent of the role of the n3-FAs in reducing the damage to organs caused by the particular drug alone. Thus, improvement in the therapeutic response of the drug therapy can improve the clinical outcome.

DETAILED DESCRIPTION

Figure 1:
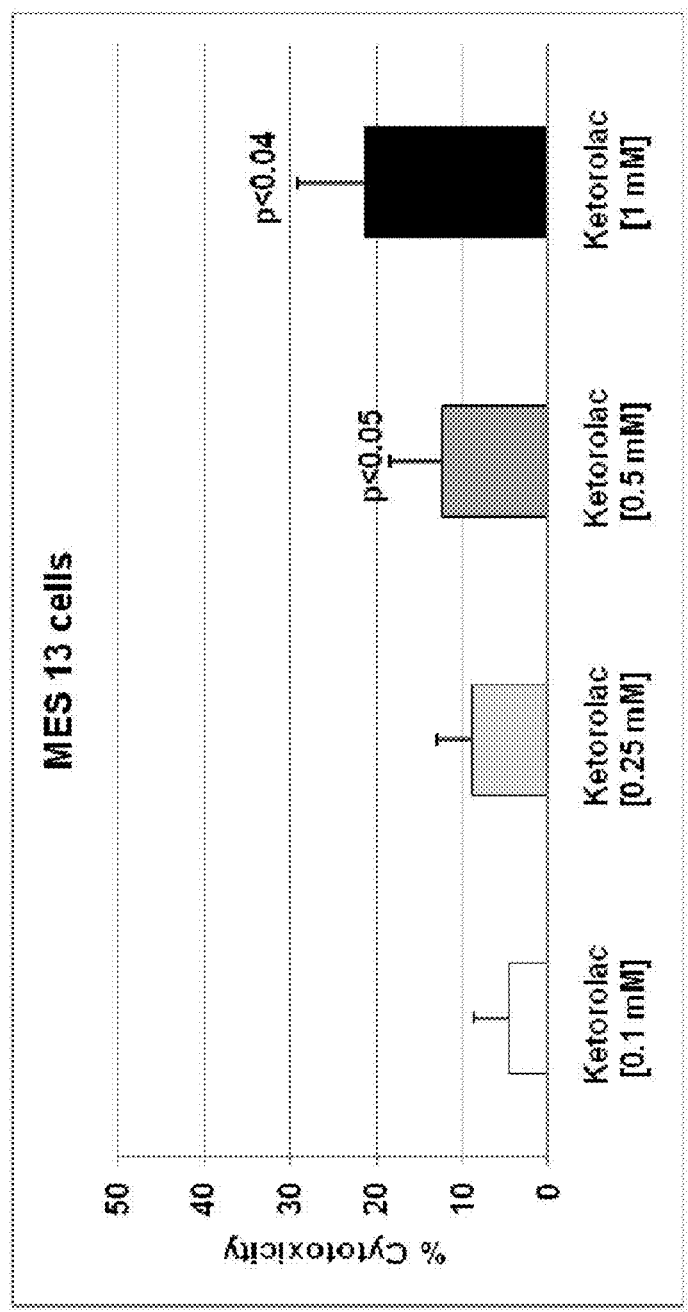
FIG. 1 shows the cytotoxic effects of 24 h treatment with Ketorolac at various concentrations on mouse intraglomerular mesangial cells (SV40 MES 13), according to an exemplary aspect.

An embodiment of the present invention is a pharmaceutical composition for parenteral administration comprising at least one omega-3 fatty acid and at least one drug.

A further preferred embodiment is a pharmaceutical composition for parenteral administration comprising a) an omega-3-fatty acid component selected from the group consisting of omega-3-fatty acid triglycerides and/or omega-3-fatty acid ester, such as omega-3 fatty acid ethyl ester; and b) at least one drug.

An exemplary embodiment is directed to a novel injectable drug dosage composition comprising: a sufficient concentration of an oil derived, for example, from fish oil triglycerides containing long-chain omega-3, or n-3, fatty acids (n3-FAs); a drug having an adverse reaction profile that is associated with damage to one or more vital organs; and a water component of an emulsion designed for intravenous injection. An exemplary composition comprises specific and concentrated bioactive n3-FAs for the purpose of addressing particular medical conditions that may be pharmaceutically related (U.S. application Ser. No. 12/382,196). For example, the bioactive n3-FAs are capable of providing safe treatment of iatrogenic causes of kidney disease, where drug-induced nephrotoxicities are mediated, in part, by reducing blood flow, i.e., ischemia, by altering the vasoconstrictive effects of thromboxane A2 (International Application No. PCT/US2010/000723).

As used herein, the term "oil-containing n3-FAs" pertains to constituents such as triglycerides that are present in marine oils, as well as constituents such as ethyl esters, which are derivatives or products obtained from transesterification of n3-FAs from triglycerides to ester forms. The source of n3-FAs, however, for a given drug formulation can be, for example, wholly natural (for example, unprocessed marine oil) or semi-synthetically derived (for example, processed marine oil). The source of n3-FAs can provide sufficient amounts of bioactive EPA, DHA and/or DPA, as, for example, attached to triglycerides or ethyl ester molecules, in order to mitigate or reduce the adverse effects of a given prescribed drug on a particular vital organ system. The beneficial pharmacological actions attributed to these bioactive n3-FAs include, for example, reductions in oxidative stress, inflammation, immune stimulation and ischemia arising from drug-related injuries.

The provision of bioactive n3-FAs, including EPA, DHA and/or DPA, and the downstream effects on prostaglandin metabolism, as well as the generation of important endogenous chemical mediators from these n3-FA precursors (for example, resolvins and protectins), can potentially have a beneficial effect on the pathophysiological effects of many diseases. This disclosure can extend these potential benefits to apply to selected drugs adversely affecting vital organs of the body. For example, substituting diets that are rich in the omega-6, or n6, fatty acids (linoleic acid and arachidonic acid) with diets rich in n3-FAs (EPA, DHA and/or DPA) can significantly alter the eicosanoid profile (2-series prostaglandins→3-series prostaglandins; 2-series thromboxanes→3 series thromboxanes; 4-series leukotrienes→5-series leukotrienes). For example, prostaglandins of the 2-series derived from n6-FAs are pro-inflammatory compared to 3-series prostaglandins derived from n3-FAs; 2-series thromboxanes obtained from n6-FAs are pro-vasoconstrictive/coagulant compared to 3-series thromboxanes obtained from n3-FAs; and 4-series leukotrienes derived from n6-FAs produce an exaggerated immune response compared to 5-series leukotrienes derived from n3-FAs.

Recent findings regarding chemical mediators (for example, resolvins and protectins) generated from n3-FAs show that the clinical benefits regarding inflammatory processes can extend beyond the initial effect. In addition, these mediators can be actively involved in reducing the extent of oxidative stress as well as facilitating the clearance of debris in the affected areas and reducing the collateral damage to surrounding tissues from an over-exuberant systemic inflammatory response resulting from various physiological causes of tissue injury (for example, infection, trauma, surgery, etc.). Oxidative stress, inflammation, stimulation of the immune response and ischemia can be significant etiological factors involved in pharmacological causes of drug-induced damage to vital organs, and supplying parenteral n3-FAs at the start of medication therapy can substantially reduce these adverse drug effects, as well as reduce or eliminate accompanying morbidity and possible mortality.

In another exemplary embodiment, the n3-FA-containing therapeutic drug vehicle can be used in combination with a prescribed drug intended for intravenous administration. Preferably, the pharmaceutical composition of the present invention is in the form of an oil in water emulsion.

Table 1 provides a broad range of exemplary oil and water ratios in exemplary compositions, along with the corresponding intakes of the bioactive n3-FAs from a 50 mL intravenous drug admixture, as typically used in the clinical setting. For example, the oil to water ratio of the composition can be from about 0.1 to 99.9 to 20.0 to 80.0. The oil to water ratio can depend on, for example, the n3-FA content of the oil phase, the particular at least one drug and marine oil employed, and the particular treatment.

According to another exemplary embodiment, intravenous therapies can provide an increased bioavailability (for example, about 100% of the administered dose) compared to other routes of administration (for example, oral, topical, intramuscular, subcutaneous, suppository, etc.) due to alterations in absorption and/or metabolism of drugs not administered directly into the systemic circulation. As such, the intravenous administration of the therapeutic drug vehicle can increase the rate of incorporation of n3-FAs into plasma membranes (for example, within hours of the infusion) and greatly accelerates the onset of the beneficial effects of n3-FAs compared to the oral, or enteral, route of administration, which can typically include days or weeks of pre-treatment with n3-FAs alone before drug therapy can commence. For example, in a conventional process, when fish oil was used as a vehicle via gastric lavage in an animal model of experimental nephrotoxicity, a 14-day pre-treatment period was necessary to achieve sufficient plasma membrane concentrations to mitigate kidney damage (Reference [9]). In a conventional process, in conditions where oral fish oil capsules have been given as therapy, for example, in patients with rheumatoid arthritis and cardiovascular disease, clinical benefits were not apparent until after several months of supplementation (Reference [31]). Thus, bioavailability, and the rapid and successful incorporation of n3-FAs into plasma cell membranes, are crucial in achieving mitigation of adverse drug events when using n3-FA-containing injectable emulsions as a therapeutic drug vehicle.

Another exemplary embodiment is directed to drug candidates prescribed intravenously, for which their use can be associated with significant adverse effects to vital organs, including mechanisms of toxicity involving oxidative stress, inflammation, immune stimulation, and ischemic insult to organ tissues (Reference [10]). By virtue of administering such drugs intravenously, the high bioavailability engendered therein can increase the toxic potential of these pharmacological agents. Vital organs of the human body can include the brain, heart, lungs, liver and kidneys. For example, the brain is known to be a lipid-rich environment, containing nerve cells and fibers protected by a lipid-containing tissue known as myelin that forms a protective sheath around neuronal structures. A risk of injury is posed by highly lipophilic drugs, such as, for example, the antiarrhythmic agent, amiodarone, a structural analog of the thyroid hormone, which can accumulate in these lipid tissues, destroying the myelin sheath and disrupting nerve conduction. These neurotoxic effects can cause peripheral neuropathy.

Other drugs acting in the central nervous system, such as, for example, levodopa, used in patients with Parkinson's disease, can benefit from n3-FAs. Long-term use of levodopa has been associated with complications in motor function (involuntary movements) that have been linked to high concentrations of arachidonic concentrations in the brain. The provision of n3-FAs can compete with the n6-FA, arachidonic acid, and are the preferred substrate for the important fatty acids in human metabolism. Thus, reducing n6-FA concentrations can be beneficial for patients with Parkinson's Disease in order to reduce the adverse effects of levodopa (Reference [11]). In another example, the anticancer drug doxorubicin, an anthracycline antibiotic, can cause acute or chronic cardiotoxicity from oxidative stress and the production of reactive oxygen species that induce damage in heart tissues. In laboratory animals, pre-treatment with n3-FA enriched diets for at least 3 weeks has been suggested to improve the therapeutic index of anthracycline antineoplastics (Reference [12]).

In another example, the antitumor drug, bleomycin, a basic glycopeptide, can induce an oxidative burden on lung tissues, which contain low levels of the drug's inactivating enzyme, bleomycin hydrolase. Increasing lung tissue levels of bleomycin can cause a release of cytokines, for example, tumor necrosis factor, and can also result in interaction with iron and molecular oxygen, which can in turn cause dangerous free radical production. In pulmonary endothelial cell cultures exposed to amiodarone, pre-treatment with n3-FAs was shown to protect against toxicity (Reference [13]). In another example, the anticonvulsant, valproic acid, a branched-chain carboxylic acid, can produce hepatic steatosis, or "fatty liver", leading to significant liver disease. In an animal model of necroinflammatory liver injury, pre-treatment with n3-FAs reduced oxidative damage and showed protective effects (Reference [14]). In yet other examples involving animals pre-treated with n3-FAs, several popular antibiotics, such as gentamicin (Reference [15]), and immunosuppressive agents, such as cyclosporine (Reference [16]) were shown to cause less kidney damage. Other drug candidates, that can cause kidney damage, for example, non-steroidal anti-inflammatory agents, including ketorolac and indomethacin, as well as ionic radiocontrast agents, can also benefit from inclusion of n3-FAs in intravenous emulsions containing those drugs or agents.

In exemplary embodiments, co-administration instead of pre-treatment with specific n3-FAs, in high concentration, and in sufficient intravenous doses, using, for example, omega-3 acid-containing marine oils as the therapeutic drug vehicle, can greatly improve the safety profile of parenterally administered drugs that presently exert adverse effects on vital organs. Pre-treatment with n3-FAs before drug therapy is not typically a reasonable option for acutely ill patients requiring drug therapy, for whom fast action can be crucial. Hence, in such cases, supplying n3-FAs through oral or enteral administration is not typically viable or practical. This advantage is especially important in cases where such drug(s) possess a narrow therapeutic index (for example, low ratio of lethal median dose to desirable median dose). The therapeutic index refers to the ratio of the dose required to produce a toxic effect and the dose needed to elicit the desired therapeutic response, and is a relative indication of the potency and safety of the drug. For example, the at least one drug having a narrow therapeutic index can exhibit a significant overlap between the effective dose and the toxic dose.

An example of a drug having a narrow therapeutic index is the aminoglycoside, gentamicin, which is a broad-spectrum parenteral antibiotic against aerobic gram-negative bacteria. An exemplary therapeutic range in plasma is between 4 to 10 µg/mL, but toxicity to the kidneys occurs when the trough blood level (the blood level before the next dose) is above 2 µg/mL. Such exemplary drug has a narrow therapeutic range and the toxicity to kidneys is associated with impaired excretion and drug accumulation.

Another example of a drug having a narrow therapeutic index is the antifungal antibiotic amphotericin B which can have a high degree of kidney toxicity, and occurs within the therapeutic dose range. Additional examples of drugs having a narrow therapeutic index include cyclosporine, ketorolac, cisplatin, the anthracycline cancer drug doxorubicin. In the case doxorubicin, a cumulative dose of >550 mg/m$^2$ can be associated with cardiomyopathy. In an exemplary embodiment, the use of n3-FAs as a therapeutic drug vehicle with these drugs having a narrow therapeutic index can mitigate the toxic responses to vital organs.

Table 2 depicts examples of possible drugs/categories that can be associated with injury to vital organs. Other drugs/categories can be included where, for example, co-administration of concentrated n3-FAs may accentuate the effects of the primary drug therapy. According to a preferred embodiment of the pharmaceutical composition the at least one drug is a material that damages a vital organ when the material is not simultaneously administered with the at least one omega-3 fatty acid, e.g. omega-3 fatty acid triglyceride and/or omega-3 fatty acid ester, such as omega-3 fatty acid ethyl ester.

The examples in Table 2 are not necessarily limiting, but rather are examples of a broad range of possible combinations and permutations.

An exemplary embodiment can employ, for example, a dose range of from about 1 to about 300 mg/kg, as well as combination(s) of n3-FAs designed to accompany a prescribed drug in a proposed intravenous formulation. Table 3 provides examples of the doses (in g of n3-FAs) across the aforementioned dose range for adult patients weighing between 40 and 100 kg. The entries in Table 3 can be applied to lower weights, such as for infants and pediatric patients, where applicable. The examples in Table 3 are not necessarily limiting, but are examples of a broad range of possible combinations and permutations.

According to an exemplary aspect, a source of n3-FAs can be naturally-occurring, semi-synthetic, synthetic, or a combination thereof. For example, a naturally-occurring source of n3-FAs can include fish oil triglycerides. A semi-synthetically-derived source of n3-FAs can include, for example, n3-FAs attached to neutral triglycerides, ethanol as ethyl esters, or a combination thereof. The source of n3-FAs can be naturally-occurring, such as from marine oil triglycerides, but may then be synthetically enriched. The sources of n3-FAs can be from a mixture of naturally-occurring and synthetically-derived products.

For example, an oil that is derived from fish oil can be used which contains n3-FAs at a concentration higher than that occurring in natural sources.

According to a preferred embodiment of the invention the pharmaceutical composition comprises omega-3-fatty acid triglycerides and medium chain triglycerides (MCT). Preferably, the pharmaceutical composition for parenteral, preferably intravenous administration, is an emulsion which comprises 10 to 69 wt.-% MCT, based on the total amount of the oil component in the emulsion.

Preferably, the medium chain triglyceride (MCT) [triglyceride obtained from esterification of glycerin with medium chain fatty acids]; comprises more than 50%, more preferably more than 80% and especially at least 95% of saturated fatty acids with 8 and 10 carbon atoms, based on the total number of esterified fatty acids in the MCT. Further, the composition of the fatty acid fraction of the MCT may comprise (based on the total number of esterified fatty acids in the MCT):

caproic acid, preferably at a maximum 2.0%; and/or
caprylic acid, preferably ranging from 50.0 to 80.0%; and/or
capric acid, preferably ranging from 20.0 to 50.0%; and/or
lauric acid, preferably up to a maximum of 3.0% and/or
myristic acid, preferably up to a maximum of 1.0%.

The oil can optionally include medium-chain fatty acids from medium chain triglycerides (MCTs), which can be saturated medium-chain fatty acids. The oil can optionally include n6-FAs such as for example, from a vegetable oil. In one embodiment, the composition such as an emulsion can be stable, has normal metabolic clearance, and/or is well-tolerated by patients. For example, the emulsion can be an oil-in-water (o/w) emulsion.

An exemplary oil is derived from fish, and can be rich in the polyunsaturated and bioactive omega-3 fatty acids. The oil component of the emulsion can contain fish oil triglycerides, for example, omega-3 acid triglycerides. The fish oil triglycerides, can be present from about 31% to about 90%, or from about 41% to about 90%, or from about 45% to about 90%, or greater than 50% to about 90%, or from about 51% to about 90%, or from about 55% to about 90%, or from about 60% to about 90%, or from about 70% to about 90%, or from about 80% to about 90%, or from about 40% to about 80%, or from about 50% to about 70%, or from about 60% to about 65%, based on the total weight of the oil component of the emulsion. For example, by employing exemplary ranges of fish oil triglycerides, the amount of esterified omega-3 fatty acids delivered to a human body can be increased. For example, Applicant has recognized the clinical significance of the absolute intake of omega-3 fatty acids, and has discovered that such absolute intake of omega-3 fatty acids can be increased by employing, for example, the exemplary ranges of fish oil triglycerides. For example, Applicants have recognized that in at least some applications, for example cardiovascular health applications, the absolute intake of omega-3 fatty acids can be a more accurate indicator of overall efficacy than the ratio of omega-3 fatty acids to omega-6 fatty acids.

They can be 20- to 22-carbon compounds and can contain 3 or more double bonds located at the 3rd position from the methyl end of the long-chain fatty acid (LCFA) molecule. Standard notation for the various fatty acids (FAs) includes: 1) carbon number, followed by, 2) the number of double bonds, and ending with 3) the position of the double bond relative to the methyl position (or "n3" in the case of the LCFA from fish oil). In particular, the marine oil can be highly enriched with two major n3-FAs, i.e., eicosapentaenoic acid, or EPA (20:5n3), and docosahexaenoic acid, or DHA (22:5n3). The marine oil can contain lesser amounts of other n3-FAs, such as docosapentaenoic acid, or DPA (22:6n3). The fish oil component of the o/w parenteral lipid emulsion can represent oils from a mixture of fatty fish families, such as from the following species: *Engraulidae* (e.g., anchovies), *Carangidae* (e.g., mackerel), *Clupeidae* (e.g., herring), *Osmeridae* (e.g., smelt), *Salmonidae* (e.g., salmon) and *Scombridge* (tuna).

In the European Pharmacopeia (EP), there are two monographs (i.e., EP 1352 entitled "Omega-3 Acid Triglycerides", and, EP 1912 entitled "Fish Oil, Rich in Omega-3 Acids") that pertain to fish oil that is acceptable for use in parenteral emulsions (EP 1352, EP 1912, 2008). The monograph EP 1352 substantially differs from EP 1912 in that the composition and requirements for the bioactive n3-FAs in EP 1352 are much higher than in EP 1912 (EP 1352: EPA+DHA≥45%; total n3-FAs≥60% vs. EP 1912: EPA: ≥13%; DHA≥9%; total n3-FAs≥28%). The levels of n3-FAs in EP 1912 are consistent with those found in nature. By comparison, in EP 1352, the n3-FA concentrations are substantially higher and can be obtained by an enrichment process such as molecular distillation, whereby certain undesirable fatty acids that are present, for example, myristic acid, palmitic acid and stearic acid, are removed. In so doing, the concentrations of all FAs present, and particularly the n3-FAs, are proportionately elevated (Reference [32]). In an exemplary embodiment, the fish oil triglycerides can include omega-3 fatty acids in an amount of at least 60%, based on the total weight of the fatty acids of the fish oil triglycerides. In an exemplary embodiment, the fish oil triglycerides can include a total amount of EPA and DHA of at least 45%, based on the total weight of the fatty acids of the fish oil triglycerides. For example, the fatty acids and omega-3 fatty acids (such as, for example, EPA and DHA) discussed herein refer to the constituent parts of such acids in a fish oil triglyceride, in accordance with EP 1352. For example, the fatty acids and omega-3 fatty acids (such as, for example, EPA and DHA) discussed above can be in their esterified form when present in the fish oil triglycerides.

According to a preferred embodiment the pharmaceutical composition of the invention comprises an omega-3-fatty acid component which comprises eicosapentaenoic acid in an amount of 30% or greater, docosahexaenoic acid in an amount of 30% or less, and docosapentaenoic acid in an amount of about 40% or less, based on the weight of the total omega-3 fatty acid content.

The fish oil triglycerides can contain at least one n6-FA, for example, a plurality of n6-FAs. The at least one n6-FA can include, for example, arachidonic acid or AA (20:4n6), linoleic acid or LA (18:2n6), alpha linolenic acid or ALA (18:3n3) or a combination thereof. For example, the total content of the at least one n6-FA can be from about 0.1% to about 1.0%, or from about 0.2% to about 0.9%, or from about 0.3% to about 0.8%, or from about 0.4% to about 0.7%, or from about 0.5% to about 0.6%, based on the weight of the oil component of the emulsion.

An exemplary second component of the oil component of the emulsion can include at least one medium chain triglyceride (MCT), for example, a plurality of MCTs. For example, the at least one MCT can be present from about 10% to about 69%, or from about 10% to about 40%, or from about 10% to about 30%, or from about 10% to about 20%, or from about 10% to about 15%, or from about 20% to about 60%, or from about 30% to about 50%, or from about 40% to about 45%, based on the total weight of the oil component of the emulsion. For example, by employing exemplary ranges of MCT, the amount of esterified omega-3 fatty acids delivered to a human body can be increased. For example, by employing exemplary MCT ranges, the amount of esterified omega-3 fatty acids delivered to a human body can be increased with usage of a relatively smaller amount of MCT, while still achieving beneficial metabolic clearance and physicochemical stability characteristics of the emulsion.

For example, the at least one MCT can include a saturated medium chain fatty acid, for example, a plurality of saturated medium chain fatty acids. In an exemplary embodiment, the MCT is a triglyceride of a fatty acid having from 6 to 12 carbon atoms. The MCT can be derived from a plant such as a vegetable, for example, a plurality of plants. The MCT can contain caprylic acid (for example, in an amount of about 50% to about 80% by weight of the MCT), an 8-carbon saturated FA (8:0). The MCT can contain capric acid (for example, in an amount of about 20% to about 50% by weight of the MCT), a 10-carbon saturated FA (10:0). For example, the medium-chain triglycerides can contain triglycerides of caprylic acid and capric acid, in an amount of at least 90% by weight of the medium-chain triglycerides. The description of the MCT for use in this disclosure can, for example, meet the requirements of EP monograph 0868, entitled "Triglycerides, Medium Chain" (Triglycerida saturate media) (EP 0868, 2008).

Determination of the content of the omega-3 fatty acids can be made as described in the European Pharmacopeia "Fish oil, rich in omega-3 acids". The content of n3-FAs can be from any single n3-FA, or any combination thereof. In an exemplary embodiment, the composition can contain EPA, DHA, DPA or a combination thereof, for example, each of EPA, DHA and DPA. The individual dosage, for example total daily dosage, of eicosapentaenoic acid (EPA) can vary from 0 to 300 mg/kg of the formulation, for example, from 50 to 250 mg/kg, for example, from 100 to 200 mg/kg, based on the body weight. The individual dosage, for example total daily dosage, of docosahexaenoic acid (DHA) can vary from 0 to 300 mg/kg of the formulation, for example, from 50 to 250 mg/kg, for example, from 100 to 200 mg/kg, based on the body weight. The individual dosage, for example total daily dosage, of docosapentaenoic acid (DPA) can vary from 0 to 300 mg/kg of the formulation, for example, from 50 to 250 mg/kg, for example, from 100 to 200 mg/kg, based on the body weight. For example, EPA, DHA and/or DPA can be present in amounts which are effective to mitigate damage to at least one vital organ which would otherwise be caused by the at least one drug.

Preferably, the pharmaceutical composition of the invention is for use in the treatment by daily parenteral administration of the omega-3 fatty acid in an amount of about 1 to about 300 mg/kg body weight.

The individual dosage of n3-FAs can be from any single n3-FA, or any combination thereof (for example containing EPA, DHA and DPA). In an exemplary embodiment, the individual total daily dosage of n3-FAs can be about 1 to about 300 mg/kg, for example, about 100 to 200 mg/kg, based on the body weight.

In another exemplary embodiment, various combinations of the bioactive n3-FAs can be present, with some therapeutic drug vehicles containing specific percentages of selected n3-FAs. In this regard, Table 4 provides a sample of possible n3-FA combinations acting as a therapeutic drug vehicle. For example, EPA can be present in an amount from about 0% to about 100%, for example, from about 30% to about 100%, based on the weight of the total content of n3-FA. For example, DHA can be present in an amount of from about 0% to about 100%, for example, from about 0% to about 30%, based on the weight of the total content of n3-FA. For example, DPA can be present in an amount of from about 0% to about 100%, for example, from about 0% to about 40%, based on the weight of the total content of n3-FA. The examples in Table 4 are not necessarily limiting, but rather are examples of a broad range of possible combinations and permutations.

It is possible in some cases that a specific prescribed drug, within the domain of a defined therapeutic dose, will benefit from or require a specific dose and/or combination of n3-FAs tailored or customized to it in order to maximize the toxicity-mitigating effects of the n3-FAs. Certain prescribed drugs within a category of pharmacological agents can benefit from a particular combination of n3-FAs, or it is possible that such a vehicle can apply to a broad range of drugs and categories, in accordance with an exemplary embodiment. Table 5 provides an example of a therapeutic drug vehicle over several small volume infusions, and the amounts of n3-FAs a patient can receive in a 24 hour period. The examples in Table 5 are not necessarily limiting, but rather are examples of a broad range of possible combinations and permutations.

The concentration of the drug in the composition and the dosage of the drug, for example, total daily dosage, can depend on various factors such as, for example, the n3-FA formulation, the drug and the specific condition being treated.

According to a preferred embodiment of the invention the pharmaceutical composition comprises the drug in an amount of about 0.005 wt.-% to about 1.5 wt.-%, based on the weight of the composition.

For example, the least one drug can be present in an amount of about 0.005% to about 1.5%, for example, about 0.1% to about 0.5%, based on the weight of the composition.

Preferably, the pharmaceutical composition is used in the treatment by daily parenteral administration of a drug in an amount of about 0.5 to about 50 mg/kg body weight.

The dosage of the drug can be in an amount of about 0.5 to about 50 mg/kg, for example, about 10 to about 30 mg/kg, based on the weight of the composition. For example, the intravenous volume of a dosage of the composition can be about 25 to about 100 mL/dose for adults, and about 1 to about 10 mL/dose for infants.

As another exemplary embodiment, the prescribed drug can be present in either the oil fraction or the water fraction of an injectable n3-FA-containing oil-in-water emulsion, depending on the physicochemical characteristics of the drug. For example, exemplary compositions and methods can provide for the drug to be entirely present in the oil fraction, entirely present in the water fraction, or present in both the oil and water fractions. For example, this approach can be counter to current practice in the pharmaceutical industry, for example, when using injectable oil-in-water emulsions as a pharmaceutical drug vehicle to safely administer water-insoluble drugs via the intravenous route of administration (Driscoll et al, 2009).

For example, water-insoluble anesthetic/sedative agent propofol, residing in the omega-6 rich oil phase of an injectable oil-in-water emulsion, is an example of conventional practice used in drug vehicle applications by pharmaceutical formulators. In contrast, in an exemplary embodiment, the omega-3 fatty acid-containing oil can function as a novel therapeutic component, as opposed to as merely a pharmaceutical (for example, carrier-only) component. Hence, its use is not limited to a particular group of drugs based on their inherent solubility and partition coefficients with respect to a particular (for example, oil or water) phase of the emulsion. In an exemplary embodiment, the omega-3 fatty acid-containing oil can serve dual purposes, for example, as both a pharmaceutical and therapeutic drug vehicle for selected pharmacological agents.

As another exemplary embodiment, the n3-FAs in a given formulation can accentuate the pharmacological actions of the primary, prescribed drug and improve the therapeutic response to drug therapy. These effects can arise from additive pharmacological effects that both complement the intended actions of the primary drug and also improve and/or accelerate the membrane altering (for example, reparative, sensitization) properties of the n3-FAs. In the first case, for example, the clinical effects of a diuretic such as the "high ceiling, loop diuretic", furosemide, whose pharmacological actions involve enhanced synthesis of vasodilatory prostaglandins that increase blood flow to the kidneys, can be enhanced by the actions of n3-FAs that form the less vasoconstrictive, thromboxane A3 series. This can be of particular clinical significance in critically ill patients who are fluid-overloaded and resistant to conventional diuretic therapy. In another example, n3-FAs can possess analgesic properties that can complement the actions of drug(s) used in pain management (Reference [18]). In the second case, for example, it has been suggested that n3-FAs can improve the response to chemotherapy of various cancers by enhanced cytotoxicity of anti-cancer drugs and by reducing oxidative stress in animal and cell culture models (References [19] to [27]) and humans (References [28] to [30]). In an exemplary embodiment, an additional benefit of using n3-FAs as a therapeutic drug vehicle can be an improvement of clinical outcomes by accentuating the response to primary drug therapy.

According to a preferred embodiment the pharmaceutical composition comprises a) an omega-3-fatty acid component selected from the group consisting of omega-3-fatty acid triglycerides and/or omega-3-fatty acid ethyl ester; and b) at least one drug for use in the treatment or prophylaxis of toxic side effects of said drug.

Further, the pharmaceutical composition of the invention can be used in mitigating toxicity effects of the drug. The toxicity effects are preferably selected from the group selected from oxidative stress, inflammation, adverse immune response, ischemia and damages of vital organs such as kidney, brain, heart, liver and lung, more preferably adverse drug effects selected from the group consisting of oxidative stress, inflammation, immune stimulation, ischemia of at least one vital organ, and a combination thereof.

In view of the complexity of the diverse actions of n3-FAs that can reduce inflammation, oxidative stress, immune modulation and ischemic injury, and the related pharmacological actions underlying the mechanisms of drug injury to vital organs, there are numerous unique exemplary aspects of this disclosure. Special interactions between n3-FAs and drugs associated with damage to vital organs can result in achieving these benefits from the onset of drug therapy by the intravenous provision of the therapeutic drug vehicle. That is, in an exemplary embodiment, the nearly complete bioavailability of the intravenous route of administration can allow rapid incorporation of n3-FAs into plasma cell membranes to exert mitigation of the toxic effects of selected drugs.

In an exemplary embodiment, having the option to provide n3-FAs in high concentrations far above the levels found in natural marine sources, using semi-synthetic methods of enrichment through attachment to triglyceride or ester molecules, can further enhance their efficient incorporation into plasma cell membranes. For example, a composition described in copending U.S. application Ser. No. 12/382,196 filed on Mar. 11, 2009, and International Application No. PCT/US2010/000723 filed on Mar. 11, 2010, the contents of which are incorporated by reference herein, can be employed in the present compositions and methods. This exemplary advantage can be particularly beneficial, because many intravenous drugs are provided in multiple doses over 24 hours via small-volume parenterals (for example, ≤100 mL). Hence, in certain cases, using wholly natural sources of fish oil, averaging approximately 30% n3-FAs in the total fatty acid profile, can benefit from or require higher volumes of lipid emulsion per day, which may not be tolerated (for example, inducing hypertriglyceridemia). Also, the use of such relatively low-n3-FA-concentration natural fish oil may be unable to reasonably and safely deliver effective n3-FA doses as a therapeutic drug vehicle at the upper limits indicated in this disclosure (for example, up to 300 mg/kg). Use of exemplary aspects can obviate the concerns associated with pretreatment with n3-FAs when other routes of administration are applied (e.g., oral or enteral).

In a preferred embodiment the pharmaceutical composition is an emulsion wherein the emulsion comprises an oil component and a water component, the oil component comprising fish oil triglycerides in an amount of about 60% to about 90% based on the weight of the oil component; wherein the fish oil triglycerides comprise omega-3 fatty acids in an amount of at least 60%, based on the total weight of the fatty acids of the fish oil triglycerides; wherein the fish oil triglycerides comprise a total amount of EPA and DHA of at least 45%, based on the total weight of the fatty acids of the fish oil triglycerides; and, at least one medium-chain triglyceride, wherein a total amount of the at least one medium-chain triglyceride is from about 10% to about 40% based on the weight of the oil component.

In an exemplary aspect, the composition employed in the method can be an emulsion comprising: an oil component and a water component, the oil component comprising: fish oil triglycerides in an amount of about 60% to about 90% based on the weight of the oil component; wherein the fish oil triglycerides comprise omega-3 fatty acids in an amount of at least 60%, based on the total weight of the fatty acids of the fish oil triglycerides; wherein the fish oil triglycerides comprise a total amount of EPA and DHA of at least 45%, based on the total weight of the fatty acids of the fish oil triglycerides; and, at least one medium-chain triglyceride, wherein a total amount of the at least one medium-chain triglyceride is from about 10% to about 40% based on the weight of the oil component.

According to another exemplary aspect, the composition employed in the method can be an emulsion comprising: an oil component and a water component, the oil component comprising: fish oil triglycerides in an amount of greater than 50% to about 90% based on the weight of the oil component of the emulsion; wherein the fish oil triglycerides comprise omega-3 fatty acids in an amount of at least 60%, based on the total weight of the fatty acids of the fish oil triglycerides; wherein the fish oil triglycerides comprise a total amount of EPA and DHA of at least 45%, based on the total weight of the fatty acids of the fish oil triglycerides; and, a medium-chain triglyceride.

According to another exemplary aspect, the composition employed in the method can be an emulsion comprising: an oil component and a water component, the oil component comprising: fish oil triglycerides in an amount of about 31% to about 90% based on the weight of the oil component of the emulsion; wherein the fish oil triglycerides comprise omega-3 fatty acids in an amount of at least 60%, based on the total weight of the fatty acids of the fish oil triglycerides; wherein the fish oil triglycerides comprise a total amount of EPA and DHA of at least 45%, based on the total weight of the fatty acids of the fish oil triglycerides; and, a medium-chain triglyceride; wherein the emulsion is an oil-in-water emulsion, and wherein the concentration of the oil component in the emulsion is 5 g/100 mL to less than 20 g/100 mL, or the concentration of the oil component in the emulsion is greater than 20 g/100 mL to 30 g/100 mL.

In an exemplary embodiment, n3-FAs can, for example, exert their beneficial effects by modifying the common mechanisms of tissue injury underlying drug toxicity to vital organs. Fourth, by reducing the toxic potential of drugs on vital organs, higher doses of certain drug(s) can be given in order to address the underlying clinical problem, which can increase the clinical efficacy of certain drug regimens in a dose-dependent manner. Fifth, in selected cases, n3-FAs can improve the therapeutic response of drugs by accentuating or complementing their mechanisms of pharmacological actions.

The therapeutic drug vehicle can exert its toxicity-mitigating effects of selected drugs by reducing oxidative stress, reducing inflammation, adverse immune responses, reducing ischemia, or a combination thereof. The composition of the n3-FA-containing therapeutic vehicle can be tailored to a specific drug, a specific dose of a drug, several drugs in the same therapeutic category, and/or several drugs spanning several therapeutic categories. The therapeutic drug vehicle can accentuate the beneficial pharmacological effects of the drug in the formulation in addition to mitigation of its toxicity. The therapeutic drug vehicle can accentuate the beneficial pharmacological effects of the drug in the formulation that can reduce the amount of drug necessary with a further mitigation in its toxicity. The therapeutic drug vehicle can improve the therapeutic response of drug therapy and thus, clinical outcome by way of its reparative properties. The therapeutic drug vehicle can be used for parenteral administration of drugs as, for example, an oil-in-water injectable emulsion so as to exert its beneficial effects at the onset of drug therapy. The addition of the drug to a therapeutic drug vehicle produced from this application can reside in either the "dispersed" or "internal" phase or in the "continuous" or "external" phase of an emulsion formulation.

In an exemplary embodiment of a method of parenterally administering the composition, the at least one omega-3 fatty acid and the at least one drug are administered simultaneously. For example, such simultaneous administration can be achieved by virtue of the at least one omega-3 fatty acid and the at least one drug being present in the same emulsion composition. Any suitable parenteral administration can be used including, for example, intravenous administration and/or intra-arterial administration.

In an exemplary embodiment, the method does not include a pretreatment process of pretreating the person with an omega-3 fatty acid prior to the step of parenterally administering the composition. For example, the pretreatment process that is excluded according to an exemplary embodiment can include the daily administration of an omega-3 fatty acid. For example, the pretreatment process that is excluded according to an exemplary embodiment is a pretreatment with an omega-3 fatty acid that occurs 1 day or more prior to administration of the composition or, for example, 3 days or more prior to administration or, for example, 7 days or more prior to administration or, for example, 14 days or more prior to administration. For example, the pretreatment process that is excluded according to an exemplary embodiment is a pretreatment with an omega-3 fatty acid that occurs 3 to 21 days prior to administration of the composition or, for example, 7 to 14 days prior to administration of the composition.

The pharmaceutical composition of the present invention can preferably further comprise pharmaceutical acceptable ingredients, especially ingredients which can be used for pharmaceutical compositions which are intravenously administered. According to a preferred embodiment the pharmaceutical composition comprises one or more emulsifiers, preferably phospholipids, especially egg lecithin.

Advantageously, the pharmaceutical compositions of the present invention additionally comprise glycerin.

Further, the composition of the present invention may comprise sodium oleate and/or pH-adjusting agents such as NaOH or HCl.

Further, preferably the pharmaceutical composition may comprise one or more antioxidants, preferably α-tocopherol.

It has been found that excellent effects can be achieved for pharmaceutical compositions comprising drugs selected from the group of antibiotics and NSAIDs, in particular wherein the drug is selected from ketorolac, a pharmaceutical acceptable salt of ketorolac and gentamicin and a pharmaceutical acceptable salt of gentamicin. A preferred embodiment of the pharmaceutical composition is an oil-in-water emulsion comprising omega-3-fatty acid triglycerides and medium chain triglycerides and a drug selected from ketorolac and gentamicin and pharmaceutical salts thereof.

Especially the pharmaceutical is suitable for use in mitigating the nephrotoxicity of a drug selected from ketorolac and gentamicin and pharmaceutical salts thereof.

According to a further preferred embodiment the pharmaceutical composition comprises at least one drug is selected from the group consisting of an amphotericin, quinolone, antineoplastic agent, amiodarone, loop diuretic, azathioprine, cyclosporine, tacrolimus, indomethacin, ketorolac and a combination thereof.

Due to the excellent toxicity mitigating effect of the omega-3 fatty acid components, preferably in combination with MCT, the pharmaceutical composition of the invention can comprise various classes of drugs. Particular good results can be achieved with a pharmaceutical composition, wherein the at least one drug is selected from the group consisting of a) Antibiotics, preferably selected from the group consisting of aminoglycosides, amphotericin, chloramphenicol, ketoconazole, macrolides, quinolones and tetracyclines, b) Antineoplastic Agents, preferably selected from the group consisting of alkylating agents, antimetabolites, and antimitotics platinum coordination complexes, c) Anti-Parkinson Agents, preferably selected from the group consisting of levodopa, pramipexole, ropinirole, rotigotine and bromocriptine, d) Cardiovascular Agents, preferably selected from the group consisting of adenosine, amiodarone, angiotensin converting enzyme (ACE) inhibitors and flecamide, e) Diuretics, preferably selected from the group consisting of loop diuretics, potassium-sparing diuretics and thiazides, f) Immunosuppressive Agents, preferably selected from the group consisting of Azathioprine, Cyclosporine, Mycophenolate and Tacrolimus, g) Psychotropics, preferably selected from the group consisting of haloperidol, monoamine oxidase inhibitors, phenothiazines, serotonin reuptake inhibitors and thioxanthines, h) Non-Steroidal Anti-Inflammatory Drugs (NSAIDs), preferably selected from the group consisting of acetaminophen, aspirin, ibuprofen, indomethacin and ketorolac; and i) Pharmaceutical acceptable salts and derivatives of the drugs a) to h).

According to a specially preferred embodiment the pharmaceutical composition comprises a Non-Steroidal Anti-Inflammatory Drug (NSAID) selected from the group consisting of acetaminophen, aspirin, ibuprofen, indomethacin, ketorolac as well as the pharmaceutical acceptable salts and derivatives thereof for use in the treatment or prophylaxis of pain or swelling or redness or fever or inflammation, especially for use in the treatment or prophylaxis of severe acute post-operative pain.

Excellent results can be achieved by a pharmaceutical composition which comprises as the drug ketorolac or a pharmaceutical acceptable salt of ketorolac, such as ketorolac tromethamine, for use in the treatment or prophylaxis of pain or swelling or redness or inflammation, especially for use in the treatment of severe acute post-operative pain. Said pharmaceutical composition shows improved effects with respect to a reduced nephrotoxicity which opens the opportunity to increase the dose to be administered.

With the pharmaceutical composition of the present invention it is generally possible to increase the dose of the drugs to be administered compared to the dose usually administered. Generally the calculation of the dose of a drug is a balance between the effectiveness of the drug and the possible toxic side effects. Due to the toxicity mitigating effect of the pharmaceutical composition of the invention the dose of the drugs can be increased while maintaining the toxicity effects low. Consequently, the drugs can be administered at higher doses and are more effective.

In an exemplary embodiment the pharmaceutical composition of the invention can be used in the treatment by daily parenteral administration of ketorolac tromethamine in a single dose of more than 60 mg, preferably more than 75 mg; and in multiple doses of more than 120 mg/day, preferably more than 150 mg/day.

According to a further preferred embodiment the pharmaceutical composition comprises acetaminophen for use in the treatment or prophylaxis of pain and/or fever.

The dose of acetaminophen to be administered to a patient can be significantly increased compared to the doses usually administered. According to a preferred embodiment the pharmaceutical composition can be used in the treatment of patients weighing 50 kg by daily parenteral administration of acetaminophen in a single dose of more than 1000 mg, preferably more than 1250 mg; and in multiple doses of more than 4000 mg/day, preferably more than 5000 mg/day.

Especially preferably the pharmaceutical composition is for use in the treatment of patients weighing less than 50 kg by daily parenteral administration of acetaminophen in a single dose of more than 15 mg/kg of body weight, preferably more than 18.75 mg/kg; and in multiple doses of more than 75 mg/kg/day, preferably more than 93.75 mg/kg/day.

According to a further preferred embodiment of the present invention the pharmaceutical composition comprises indomethacin or a pharmaceutical acceptable salt of indomethacin, more preferably for use in the treatment for closing a hemodynamically significant patent ductus arteriosus in premature infants weighing between 500 g and 1750 g, especially when usual medical management is ineffective. Especially for the treatment of infants a well balanced but effective doses regime is advisable. Therefore, in a preferred embodiment the pharmaceutical composition comprises indomethacin or a pharmaceutical acceptable salt of indomethacin for use in the treatment of premature infants weighing between 500 g to 1750 g by parenteral administration of three intravenous courses at 12 to 24 hour intervals with the first dose of more than 0.2 mg/kg, preferably more than 0.25 mg/kg and a total dose of up to more than between 0.4 mg/kg and 0.7 mg/kg, preferably more than between 0.5 mg/kg and 0.875 mg/kg.

Antibiotics and especially amionoglycoside antibiotics are especially preferred drugs. There is a huge demand for antibiotics which are highly effective, in particular antibiotics which are effective against multi resistant bacteria strains. In the prior art the administration dose and effectiveness of antibiotics is limited due to toxic side effects. However, the preferred pharmaceutical composition of the present invention comprising antibiotics are more effective since a higher dose can be administered due to the toxicity mitigating effect of the composition. In a preferred embodiment the pharmaceutical composition comprises an aminoglycoside antibiotic selected from the group consisting of amikacin, gentamicin, tobramycin and pharmaceutical acceptable salts thereof, preferable for use in the treatment and prophylaxis of infections.

Preferably, the pharmaceutical composition comprises amikacin or a pharmaceutical acceptable salt of amikacin, such as amikacin sulfate, for use in the treatment and prophylaxis of infections, especially infections with multi-drug-resistant Gram negative bacteria such as *Pseudomonas aeruginosa, Acinetobacter, Enterobacter, Serratia marcescens* and *Providencia stuartii* or for use in the treatment or prophylaxis of non-tubercular mycobacterial infections and tuberculosis. In an exemplary embodiment the pharmaceutical composition is for use in the treatment by daily parenteral administration of amikacin sulfate in a dose higher than 15 mg/kg body weight, preferably more than 20.25 mg/kg body weight.

According to a further preferred embodiment the pharmaceutical composition comprises as drug gentamicin or a pharmaceutical acceptable salt of gentamicin, such as gentamicin sulfate, for use in the treatment or prophylaxis of infections, especially systemic and urinary-tract-infection, life-threatening infections, chest-infections, bacteraemia, septicaemia, severe neonatal infections, more especially infections by *Escherichia coli, Klebsiella* spp., *Proteus* spp., *Pseudomonas aeruginosa, Staphylococci, Enterobacter* spp., *Citrobacter* spp. and *Providencia* spp. Especially, the pharmaceutical composition is for use in the treatment by daily parenteral administration of gentamicin sulfate in a single dose of more than 160 mg/kg body weight, preferably more than 224 mg/kg body weight; and in multiple doses of more than 5 mg/kg body weight/day, preferably more than 7 mg/kg body weight/day.

According to a further preferred embodiment the pharmaceutical composition comprises Tobramycin or a pharmaceutical acceptable salts of Tobramycin, preferably for use in the treatment of infections, especially central nervous system infections including meningitis, septicaemia, and neonatal sepsis or gastro-intestinal infections including peritonitis or urinary tract infections such as pyelonephritis and cystitis or lower respiratory tract infections, including pneumonia, bronchopneumonia and acute bronchitis or skin, bone and soft tissue infections including burns. Preferably, the pharmaceutical composition is for use in the treatment by daily parenteral administration of tobramycin in a single dose higher than 5 mg/kg body weight, preferably more than 6.75 mg/kg body weight; and in multiple doses of more than 20 mg/kg body weight/day, preferably more than 27 mg/kg body weight/day.

According to a further preferred embodiment the pharmaceutical composition comprises amiodarone or a pharmaceutical acceptable salt of amiodarone, such as amiodarone hydrochloride, preferably for use in the treatment or prophylaxis of cardiac arrhythmia or Wolff-Parkinson-White syndrome, especially tachyarrhythmias selected from the group consisting of supraventricular tachycardias, nodal tachycardias, ventricular tachycardias, atrial flutter, atrial fibrillation and ventricular fibrillation. Preferably, the pharmaceutical composition is for use in the treatment by daily parenteral administration of amiodarone hydrochloride in a dose over the first 24 hours of more than 1000 mg, preferably more than 1250 mg; and more than 720 mg as maintenance infusion over 24 hours, preferably more than 900 mg over 24 hours.

According to a further embodiment the pharmaceutical composition of the invention comprises at least one drug is selected from the group consisting of an antineoplastic agents for use in reducing the toxicity to vital organs.

In an exemplary embodiment the pharmaceutical composition comprises at least one drug which is selected from the group consisting of antineoplastic agents for use in enhancing the toxicity against tumor cells.

Especially preferred is a pharmaceutical composition, wherein the at least one drug is selected from the group consisting of an antineoplastic agents for use in simultaneously reducing the toxicity of the drug and enhancing its toxicity against tumor cells, preferably for use in the treatment of cancer.

TABLE 1

Examples of various Emulsion Mixtures (Oil:Water or O:W Ratios) and Corresponding n3-FA Intakes from a 50 mL Small-Volume Drug Admixture Dose n3-FA Content of the Oil Phase

| O:W Ratio (g of oil/dose) | 20% | 40% | 60% | 80% | 100% |
|---|---|---|---|---|---|
| | | | (g of n3-FA/dose) | | |
| 0.1:99.9 (0.05) | 0.01 | 0.02 | 0.03 | 0.04 | 0.05 |
| 0.5:99.5 (0.25) | 0.05 | 0.10 | 0.15 | 0.20 | 0.25 |
| 1.0:99.0 (0.50) | 0.10 | 0.20 | 0.30 | 0.40 | 0.50 |
| 5.0:95.0 (2.50) | 0.50 | 1.00 | 1.50 | 2.00 | 2.50 |
| 10.0:90.0 (5.0 g) | 1.00 | 2.00 | 3.00 | 4.00 | 5.00 |
| 15.0:85.0 (7.5 g) | 1.50 | 3.00 | 4.50 | 6.00 | 7.50 |
| 20.0:80.0 (10 g) | 2.00 | 4.00 | 6.00 | 8.00 | 10.00 |

TABLE 2

Examples of Potential Drugs/Categories Affecting Vital Organs That May Benefit From n3-FA Damage Mitigation Therapy 1. Antibiotics
   a. aminoglycosides
   b. amphotericin
   c. chloramphenicol
   d. ketoconazole
   e. macrolides
   f. quinolones
   g. tetracyclines
2. Antineoplastic Agents
   a. alkylating agents
   b. antimetabolites
   c. antimitotics platinum coordination complexes
3. Anti-Parkinson Agents
   a. levodopa TABLE 2-continued Examples of Potential Drugs/Categories Affecting Vital Organs That May Benefit From n3-FA Damage Mitigation Therapy b. pramipexole
   c. ropinirole
   d. rotigotine
   e. bromocriptine
4. Cardiovascular Agents
   a. adenosine
   b. amiodarone
   c. angiotensin converting enzyme (ACE) inhibitors
   d. flecainide
5. Diuretics
   a. loop diuretics
   b. potassium-sparing diuretics
   c. thiazides
6. Immunosuppressive Agents
   a. Azathioprine
   b. Cyclosporine
   c. Mycophenolate
   d. Tacrolimus
7. Non-Steroidal Anti-Inflammatory Drugs (NSAIDs)
   a.. acetaminophen
   b. aspirin
   c. ibuprofen
   d. indomethacin
   e. ketorolac
8. Psychotropics
   a. haloperidol
   b. monoamine oxidase inhibitors
   c. phenothiazines
   d. serotonin reuptake inhibitors
   e. thioxanthines

TABLE 3

Intakes of n3-FAs (g/dose) Ranging from 1 to 100 mg/kg n3-FA Dose Range, mg/kg

| Adult Patient Weight, kg | 1 | 10 | 50 | 100 |
|---|---|---|---|---|
| | | g n3-FA/body weight | | |
| 40 | 0.04 | 0.4 | 2.0 | 4.0 |
| 50 | 0.05 | 0.5 | 2.5 | 5.0 |
| 60 | 0.06 | 0.6 | 3.0 | 6.0 |
| 70 | 0.07 | 0.7 | 3.5 | 7.0 |
| 80 | 0.08 | 0.8 | 4.0 | 8.0 |
| 90 | 0.09 | 0.9 | 4.5 | 9.0 |
| 100 | 0.10 | 1.0 | 5.0 | 10.0 |

TABLE 4

Sample of Potential n3-FAs and Dose Ranges (% of n3-FA Oil Profile) as Therapeutic Drug Vehicles

| EPA | DHA | DPA |
|---|---|---|
| 100 | 0 | 0 |
| 80 | 20 | 0 |
| 60 | 40 | 0 |
| 40 | 60 | 0 |
| 20 | 80 | 0 |
| 0 | 100 | 0 |
| 0 | 80 | 20 |
| 0 | 60 | 40 |
| 0 | 40 | 60 |
| 0 | 20 | 80 |
| 0 | 0 | 100 |
| 20 | 0 | 80 |
| 40 | 0 | 60 |
| 60 | 0 | 40 |
| 80 | 0 | 20 |
| 10 | 80 | 10 |
| 20 | 60 | 20 |
| 30 | 40 | 30 |

TABLE 4-continued

Sample of Potential n3-FAs and Dose Ranges (% of n3-FA Oil Profile) as Therapeutic Drug Vehicles

| EPA | DHA | DPA |
|---|---|---|
| 40 | 30 | 30 |
| 60 | 20 | 20 |
| 10 | 10 | 80 |
| 20 | 20 | 60 |
| 20 | 40 | 40 |
| 30 | 30 | 40 |

TABLE 5

Small-Volume Parenteral Infusions and n3-FA Intakes Using a 10% Oil-in-Water Emulsion with 50% n3-FAs in the Oil Phase Infusions per Day

| Infusion Volume | 1 | 2 | 3 | 4 |
|---|---|---|---|---|
| | | (g n3-FA) | | |
| 1 mL | 0.05 | 0.10 | 0.15 | 0.20 |
| 5 mL | 0.25 | 0.50 | 0.75 | 1.00 |
| 10 mL | 0.50 | 1.00 | 1.50 | 2.00 |
| 25 mL | 1.25 | 2.50 | 3.75 | 5.00 |
| 50 mL | 2.50 | 5.00 | 7.50 | 10.00 |

Cytotoxicity Study:

I. Cell Lines and Culture Conditions

In vitro experiments were performed using the SV 40-transformed mouse mesangial cells, [SV40 MES 13 (CRL-1927™)]. The cell line were purchased from the American Type Culture Collection (ATCC-LGC Standards GmbH, Wesel, Germany). SV40 MES 13 cells were cultured in ATCC complete growth medium: the basic medium for this cell line is a 3:1 mixture of ATCC-formulated Dulbecco's Modified Eagle's Medium [ATCC (DMEM)], and Ham's F12 medium (PAA Laboratories GmbH, Colbe, Germany) with 14 mM HEPES, supplemented with 5% fetal bovine serum (FBS), 100 U/ml penicillin, 0.1 mg/ml streptomycin. Under these culture conditions the SV40 MES 13 retained many of the differentiated characteristics of intraglomerular mesangial cells. Cells were maintained at 37° C. in a humidified atmosphere of 5% $CO_2$ and 95% air; the medium was changed every 48 h.

II. Substances Under Test

The following stock emulsions have been prepared:

TABLE 6

Emulsion LO-3 5/5

| Component | Amount per 1000 ml |
|---|---|
| Medium chain triglyceride[1] | 100 g |
| Omega-3 fatty acid triglyceride[2] | 100 g |
| Egg lecithin | 12 g |
| Glycerin | 25 g |
| Sodium oleate | 0.3 g |
| alpha-tocopherol | 0.2 g |
| NaOH | max. 0.06 g |
| water | ad 1000 ml |

TABLE 7

Emulsion LO-3 7/3

| Component | Amount per 1000 ml |
|---|---|
| Medium chain triglyceride[1] | 60 g |
| Omega-3 fatty acid triglyceride[2] | 140 g |
| Egg lecithin | 12 g |
| Glycerin | 25 g |
| Sodium oleate | 0.3 g |
| alpha-tocopherol | 0.2 g |
| NaOH | max. 0.06 g |
| water | ad 1000 ml |

TABLE 8

Emulsion LO-3 9/1

| Component | Amount per 1000 ml |
|---|---|
| Medium chain triglyceride[1] | 20 g |
| Omega-3 fatty acid triglyceride[2] | 180 g |
| Egg lecithin | 12 g |
| Glycerin | 25 g |
| Sodium oleate | 0.3 g |
| alpha-tocopherol | 0.2 g |
| NaOH | max. 0.06 g |
| water | ad 1000 ml |

[1]Medium chain triglyceride (MCT) [triglyceride obtained from esterification of glycerine with medium chain fatty acids;
minimum 95% of saturated fatty acids with 8 and 10 carbon atoms;
Composition of the fatty acid fraction:
caproic acid: maximum 2.0%
caprylic acid: 50.0 to 80.0%,
capric acid: 20.0 to 50.0%,
lauic acid: maximum 3.0% and
myristic acid: maximum 1.0%
[2]Fish oil derived Omega-3 fatty acid triglyceride in accordance with the European Pharmacopeia 1352: Mixture of mono-, di- and triesters of omega-3 acids with glycerol containing mainly triesters and obtained either by esterification of concentrated and purified omega-3 acids with glycerol or by transesterification of the omega-3 acid ethyl esters with glycerol. The origin of the omega-3 acids is the body oil from fatty fish species coming from families like Engraulidae, Carangidae, Clupeidae, Osmeridae, Salmonidae and Scombridae. The content:
sum of the contents of the omega-3 acids EPA and DHA, expressed as triglycerides: minimum 45.0%
total omega-3 fatty acids, expressed as triglycerides: minimum 60.0%.

A omega-6 fatty acid long chain triglyceride containing oil is reflected in Table 9.

TABLE 9

Emulsion O-6-LCT

| Component | Amount per 1000 ml |
|---|---|
| Soy oil | 200 g |
| Egg lecithin | 12 g |
| Glycerin | 25 g |
| Sodium oleate | 0.3 g |
| alpha-tocopherol | 0.2 g |
| NaOH | max. 0.06 g |
| water | ad 1000 ml |

Figure 6:
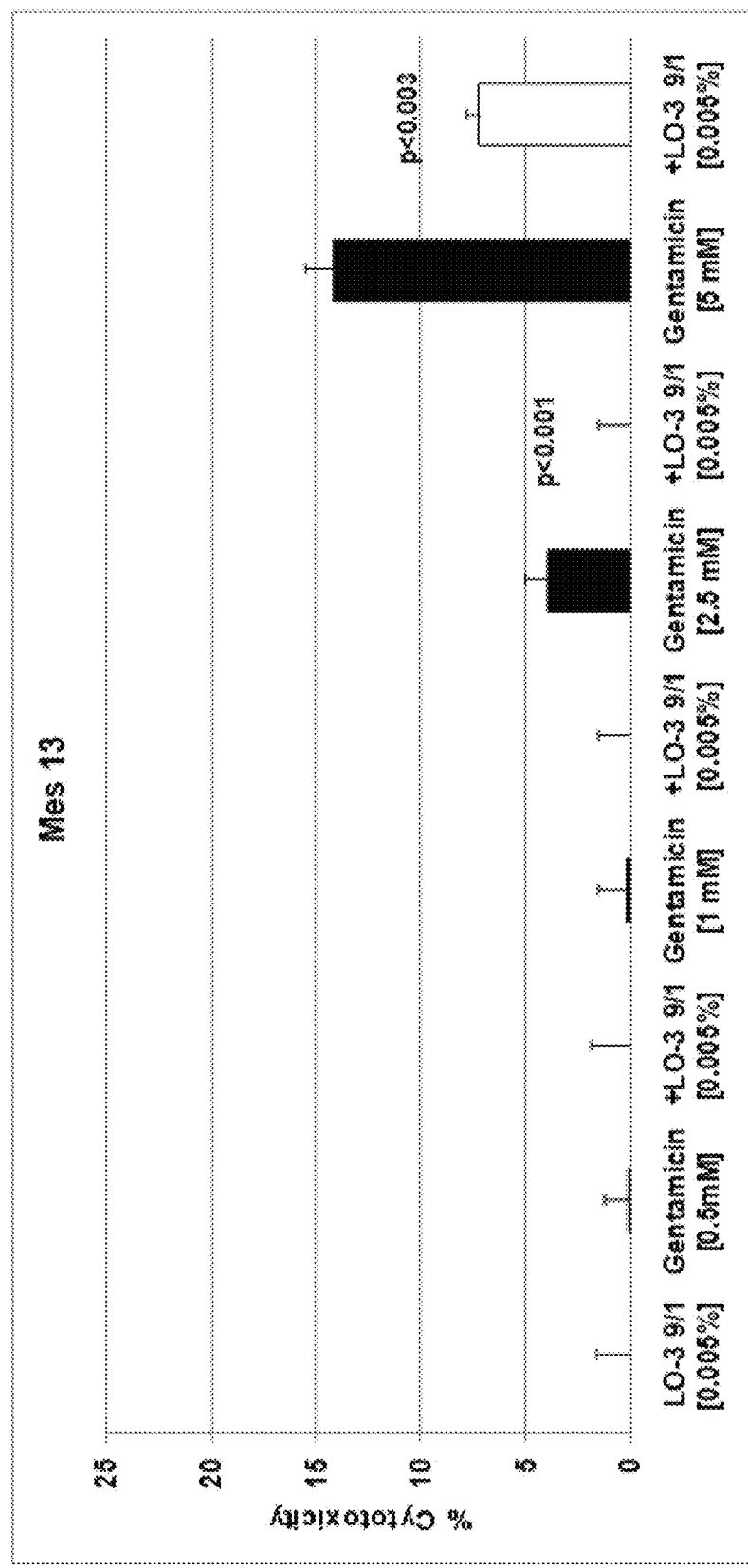
FIG. 6 shows the effects of 48 h treatment with 0.005% concentration of LO-3 9/1 on cytotoxic effect of Gentamicin in mouse intraglomerular mesangial cells (SV40 MES 13), according to an exemplary aspect.

As shown in FIG. 2 A-C, FIG. 3 A-C, FIG. 4 A-D and FIG. 6 the stock solutions (20%) reflected in Tables 6 to 9 have been diluted to the concentration specified in said Figures. The concentration mentioned in said Figures refers to the concentration of the sum of the oil components, i.e. MCT and omega-3 fatty acid triglyceride and soya oil respectively in the composition.

As an exemplary drug out of the list of NSAIDs ketorolac tromethamine is tested. The following formulation has been used and tested at various concentrations (see FIG. 1 to FIG. 4):

Ketorolac Tromethamine Injection, USP, I.V./I.M. 30 mg/ml (Hospira, Inc., Lake Forest USA).

As an exemplary drug out of the list of antibiotics the aminoglycoside gentamicin is tested. The following formulation has been used and tested of various concentrations (see FIG. 5 and FIG. 6).

Gentamicin solution, 50 mg/ml, G1397 (Sigma-Aldrich, Saint Louis USA).

Assay Methods

In this experimental part and the Figures the drug "ketorolac tromethamine" will simply be called "ketorolac".

Determination of cytotoxic concentrations of Ketorolac or Gentamicin $2-4\times10^3$ SV40 MES 13 cells in 100 µl medium/well were seeded in 96-well plates (BD Falcon™, Becton Dickinson GmbH, Heidelberg, Germany). After 48 h, the medium was changed and different concentrations of Ketorolac (0.1-1 mM) or Gentamicin (0.5-5 mM) were tested after 24 h treatment, cytotoxicity was measured as described below (see "determination of cell cytotoxicity"). As a control (=0% cytotoxicity), cells cultured with medium alone, without additional treatment with Ketorolac or Gentamicin we used.

Determination of the Cytotoxicity Mitigating Effect of the Tested Emulsions Against Cytotoxic Effects of Ketorolac or Gentamicin $4\times10^3$ SV40 MES 13 were seeded in 100 µl medium/well in 96-well plates (BD Falcon™, Becton Dickinson GmbH, Heidelberg, Germany. After 48 h, the medium was changed and 50 µl/well medium was added. Immediately the test emulsions (Table 6 to 9) were dissolved in medium and 50 µl/well at concentrations of 0.005%, 0.01% or 0.02% have been added to the cells. As a negative control, we used cells, which received 50 µl medium without any test emulsions. After 24 h incubation with the above mentioned test emulsions, the following concentrations of Ketorolac or Gentamicin were added to the MES 13 cells which were incubated additionally for 24 h: 0.25 mM, 0.5 mM or 1 mM or 0.5 mM, 1 mM, 2.5 mM or 5 mM respectively. The different concentrations of Ketorolac or Gentamicin were added to the cells either pre-treated (24 h) with test emulsions (protective effect) or without pre-treatment (cytotoxicity of Ketorolac or Gentamicin [control]). Additional controls were performed: cells pre-treated with test emulsions, however without Ketorolac or Gentamicin (control of the effect of the test emulsion) as well as cells without pre-treatment of the test emulsion and without Ketorolac or Gentamicin (=0% cytotoxicity).

Determination of Cell Cytotoxicity

Cell cytotoxicity was assesed using PrestoBlue™ reagent (Invitrogen-Life Technologies GmbH, Darmstadt, Germany). PrestoBlue™ reagent is a resazurin-based solution that functions as a cell viability indicator by using the reducing power of living cells to quantitatively measure the viability. When added to cells, the PrestoBlue™ reagent—containing a non-fluorescent, cell-permeant compound—is modified by the reducing environment of the viable cells, becoming highly fluorescent, which can be detected using fluorescence or absorbance measurements (Reference [1]). PrestoBlue™ reagent is more sensible than alamarBlue, which is a redox indicator of enzyme activity widely used in whole organism screening (Reference [2]) and is extensively used in screening test of viability and cytotoxicity (Reference [2-6]). PrestoBlue™ was directly added to the cells into the culture medium at a final concentration of 10%. Thereafter the plates were returned to the incubator. 30 min, 1 h, 2 h, 3 h and 4 h after addition of PrestoBlue™ the optical density (OD) was measured at 570 nm and 600 nm (as reference) with a SUNRISE ELISA-reader (Tecan, Salzburg, Austria). Results are expressed in % of cytotoxicity [100--($OD_{570/600}$ of samples× 100/$OD_{570/600}$ of control without substances)]. The SigmaPlot software was used to carry out statistical analyses by the unpaired Student's t test. Data are shown as mean±SEM. A p value <0.05 was considered as statistically significant.

FIGS. 1 to 6 shows the results of the Cytotoxicity measurements.

FIG. 1 demonstrates the cytotoxic effects of 24 h treatment with Ketorolac at various concentrations on mouse intraglomerular mesangial cells (SV40 MES 13). Values [in % cytotoxicity of cells without treatment (=control, =0% cytotoxicity)] are given as mean±SEM; p, significance vs. cells without treatment (=control).

In each of the FIGS. 2A-C, 3A-C, 4A-D and 6 from left to right the columns have the following meaning:

first column: shows the cytotoxicity of the pure emulsion at the specified concentration without the drug.

second column: shows the cytotoxicity of the drug at the specified concentration without the emulsion.

third column: shows the cytotoxicity of the composition consisting of the emulsion at the specified concentration and the drug with the concentration as specified in the second column.

forth column: shows the cytotoxicity of the drug of the specified concentration without the emulsion.

fifth column: shows the cytotoxicity of the composition consisting of the emulsion at the specified concentration and the drug with the concentration as specified in the forth column.

sixth column: shows the cytotoxicity of the drug at the specified concentration without the emulsion.

seventh column: shows the cytotoxicity of the composition consisting of the emulsion at the specified concentration and the drug with the concentration as specified in the sixth column.

Figure 2A:
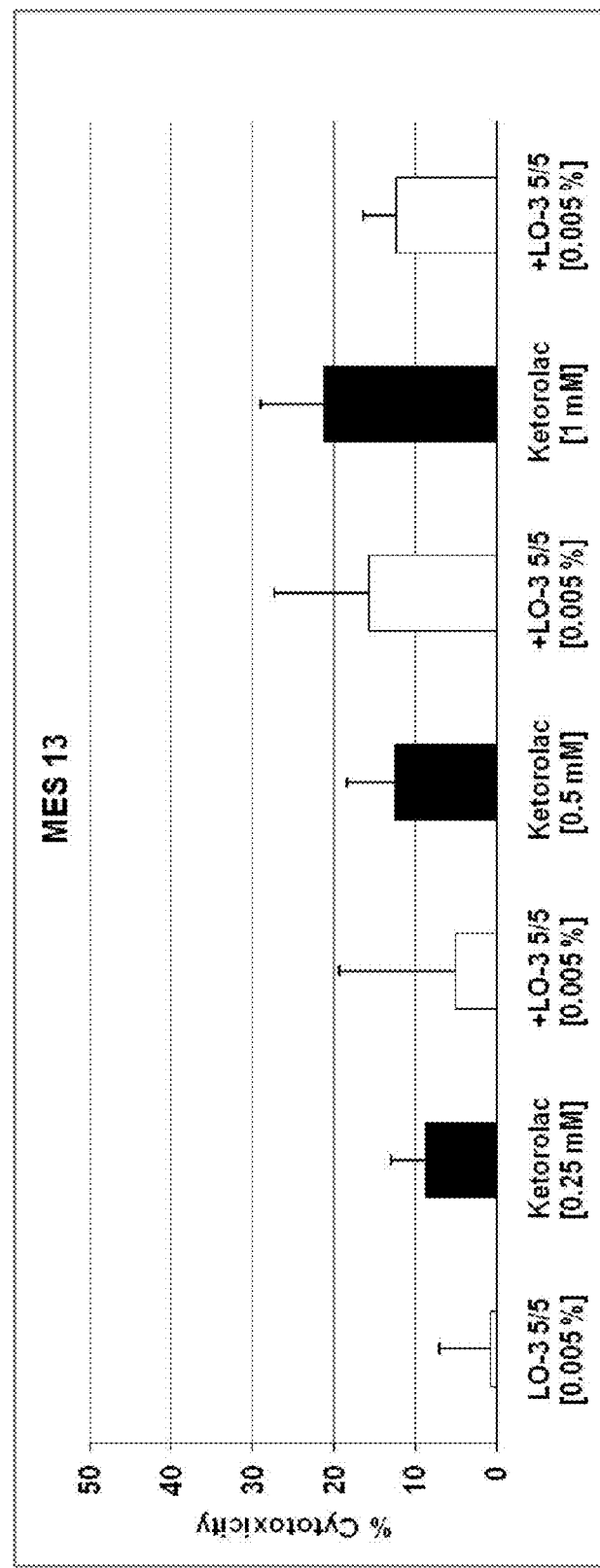
FIGS. 2A to 2C show the effects of 48 h treatment with 0.005% concentrations of LO-3 5/5 (FIG. 2A), LO-3 7/3 (FIG. 2B) and LO-3 9/1 (FIG. 2C) on cytotoxic effect of Ketorolac in mouse intraglomerular mesangial cells (SV40 MES 13), according to an exemplary aspect.
Figure 2B:
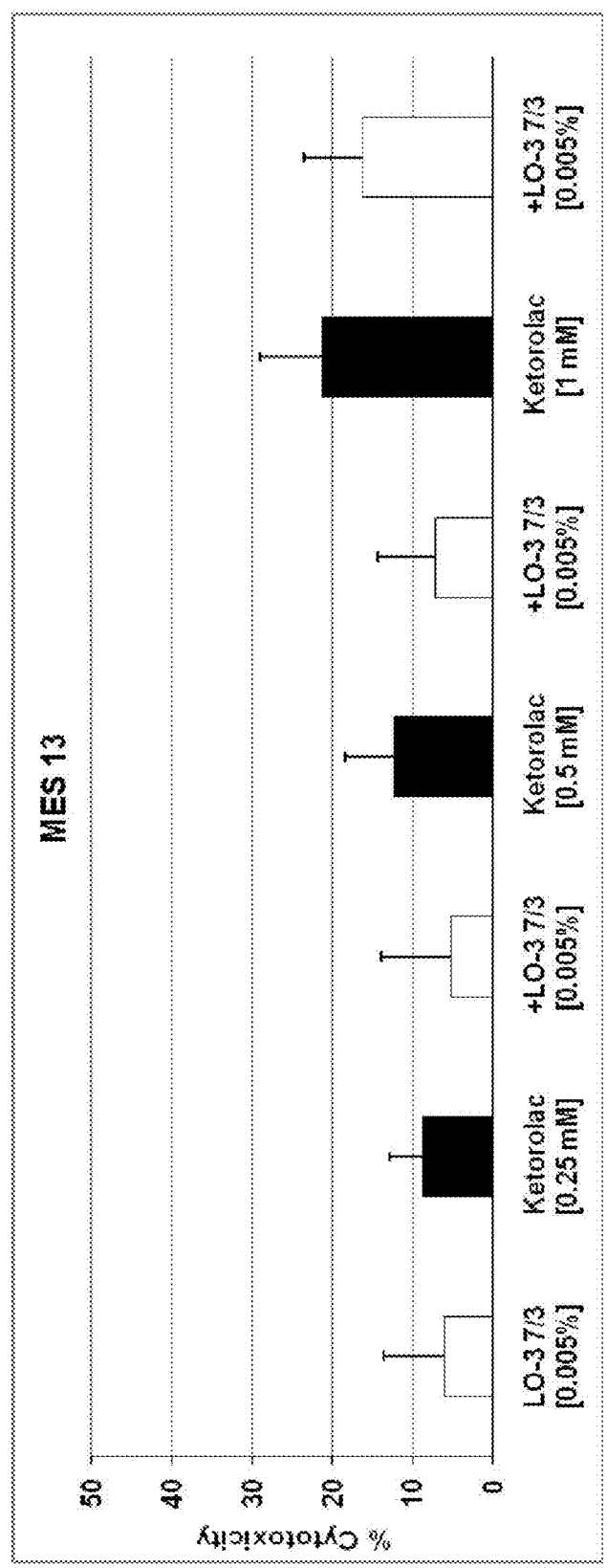
Figure 2C:
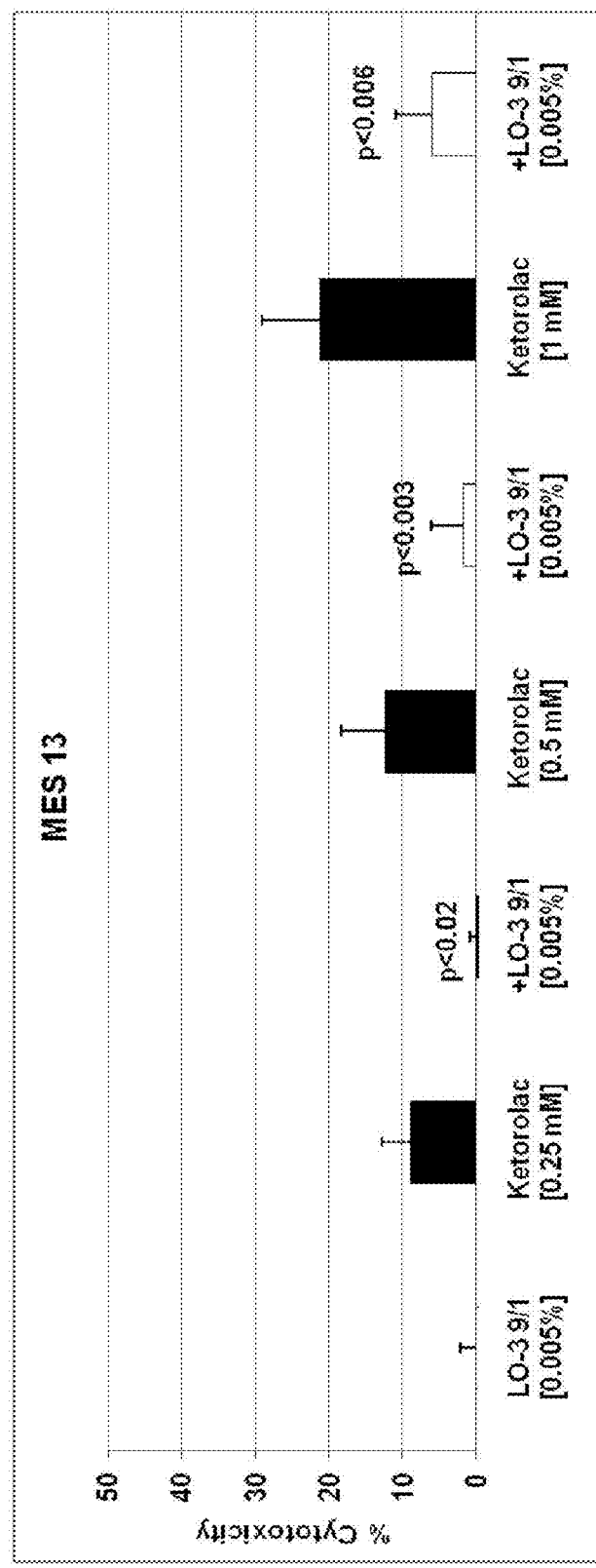

FIGS. 2A to 2C show the effects of 48 h treatment with 0.005% concentrations of LO-3 5/5 (FIG. 2A), LO-3 7/3 (FIG. 2B) and LO-3 9/1 (FIG. 2C) on cytotoxic effect of Ketorolac in mouse intraglomerular mesangial cells (SV40 MES 13). Values [in % cytotoxicity of cells without treatment (=control, =0% cytotoxicity)] are given as mean±SEM; p, significance vs. Ketorolac treatment; n=4 independent experiments, using 4-6 wells per treatment and experiment.

Figure 3A:
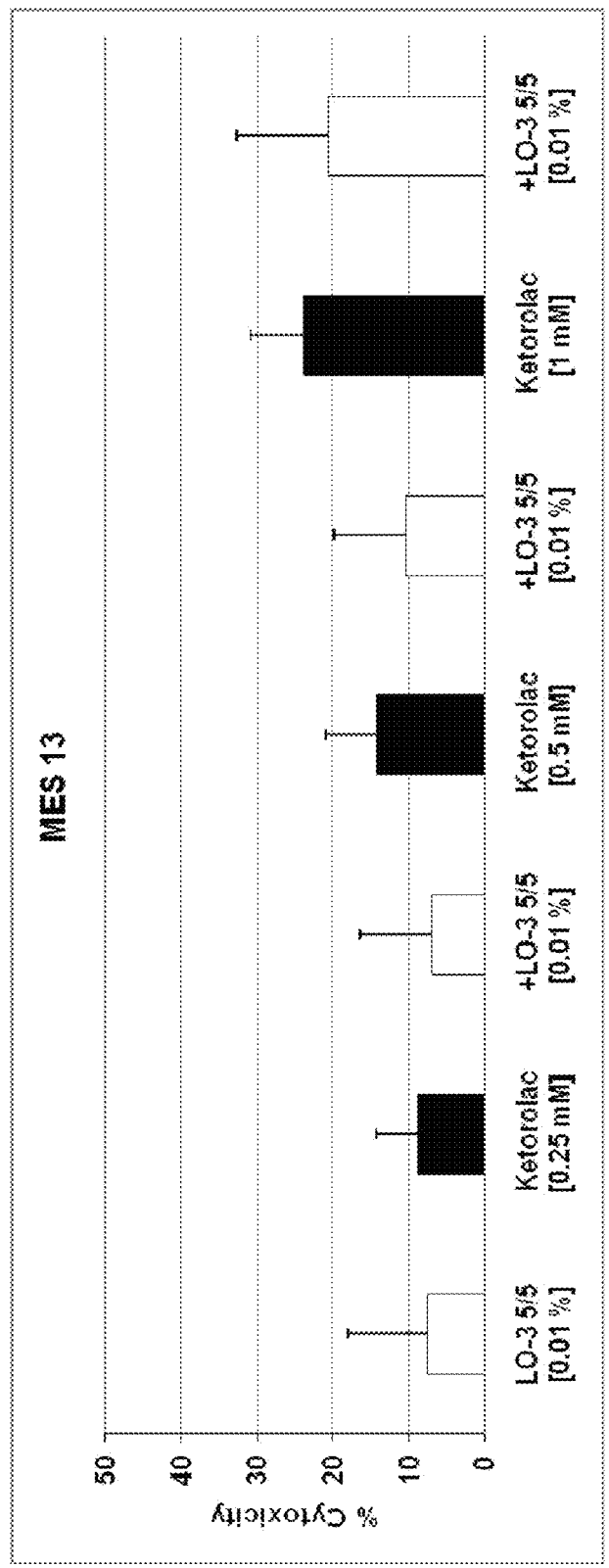
FIGS. 3A to 3C show the effects of 48 h treatment with 0.01 concentration of LO-3 5/5 (FIG. 3A), LO-3 7/3 (FIG. 3B) and LO-3 9/1 (FIG. 3C) on cytotoxic effect of Ketorolac in mouse intraglomerular mesangial cells (SV40 MES 13), according to an exemplary aspect.
Figure 3B:
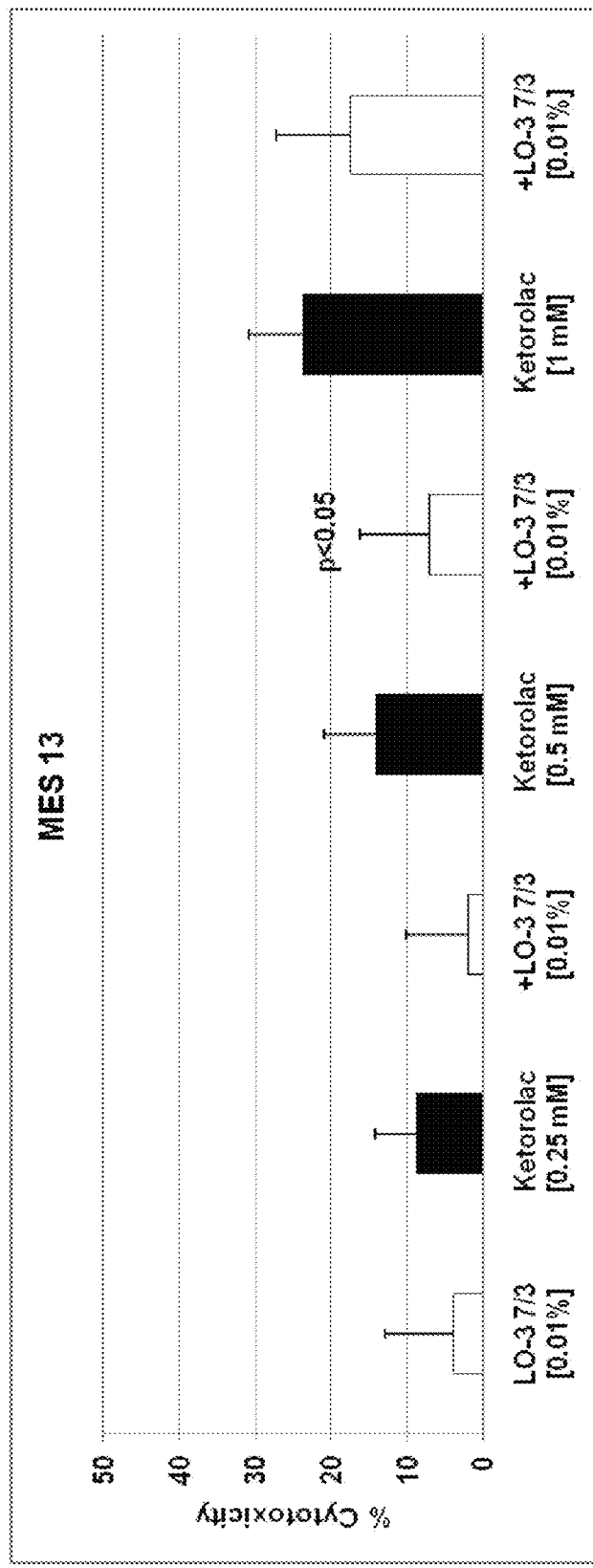
Figure 3C:
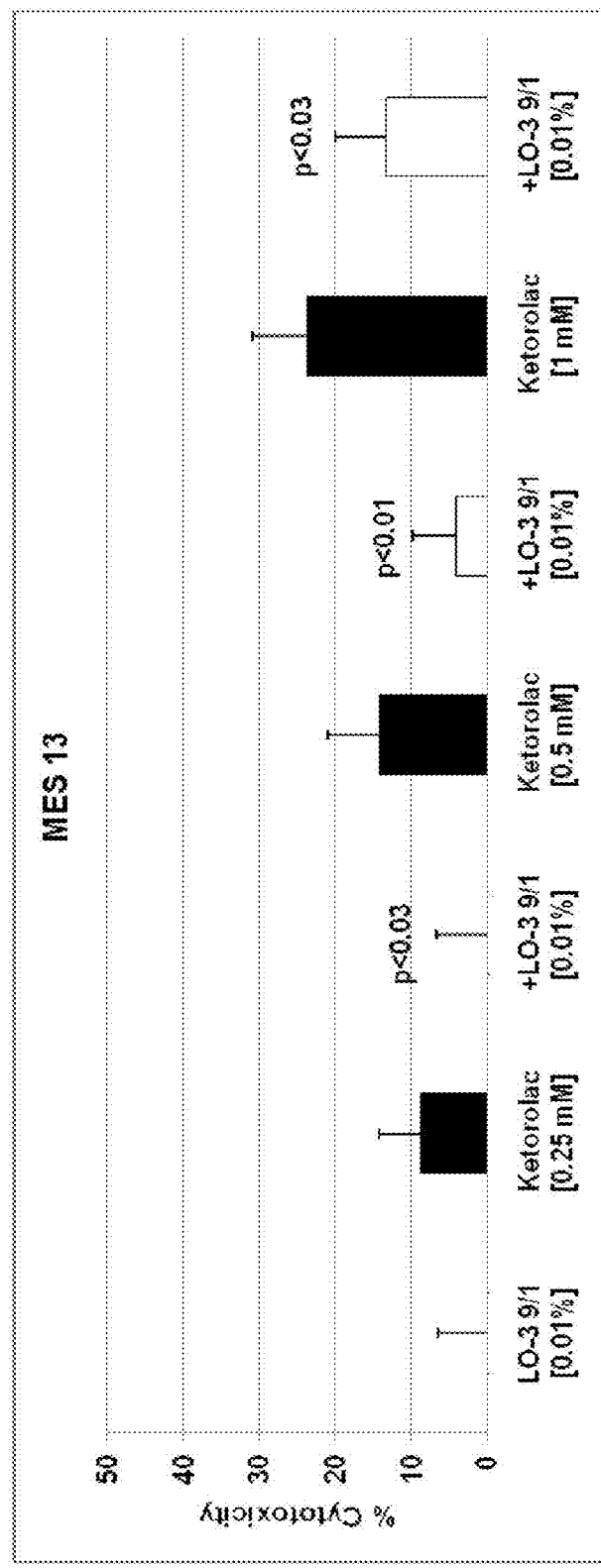
Figure 4A:
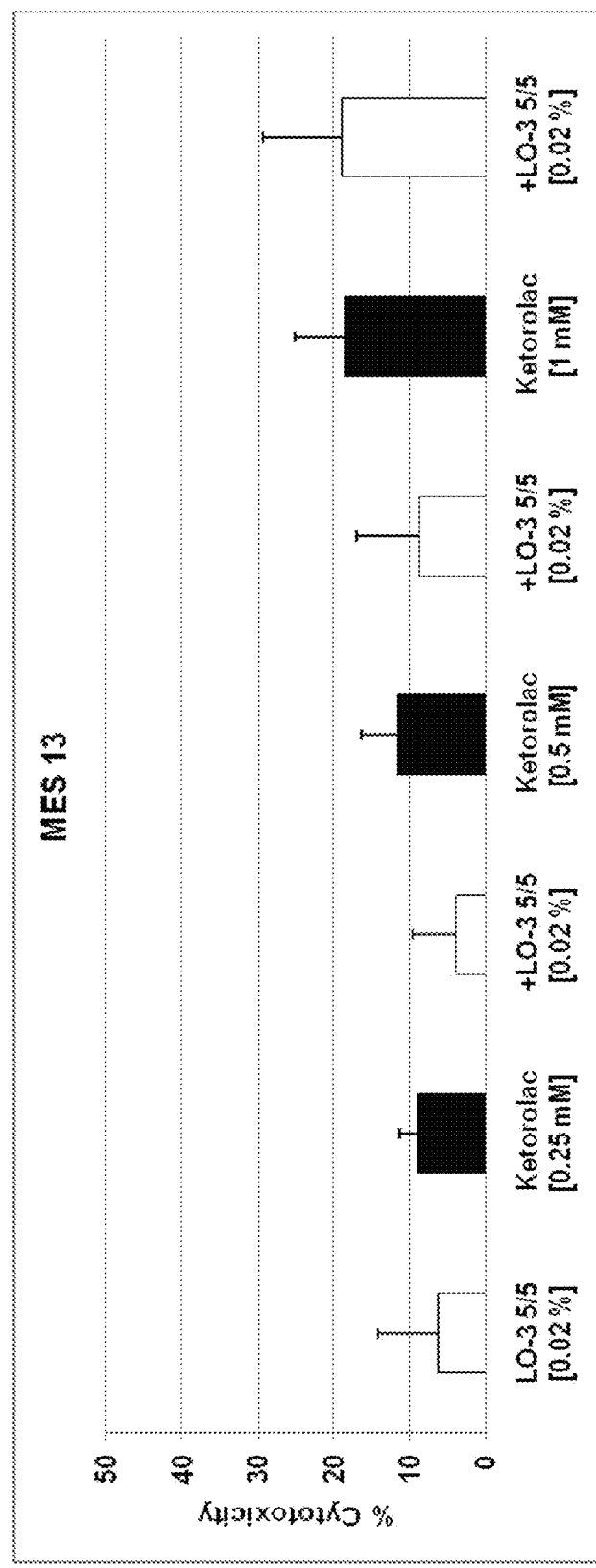
FIG. 4A to 4D show the effects of 48 h treatment with 0.02 concentration of LO-3 5/5 (FIG. 4A), LO-3 7/3 (FIG. 4B), LO-3 9/1 (FIG. 4C) and O-6-LCT (FIG. 4D; comparative) on cytotoxic effect of Ketorolac in mouse intraglomerular mesangial cells (SV40 MES 13), according to an exemplary aspect.
Figure 4B:
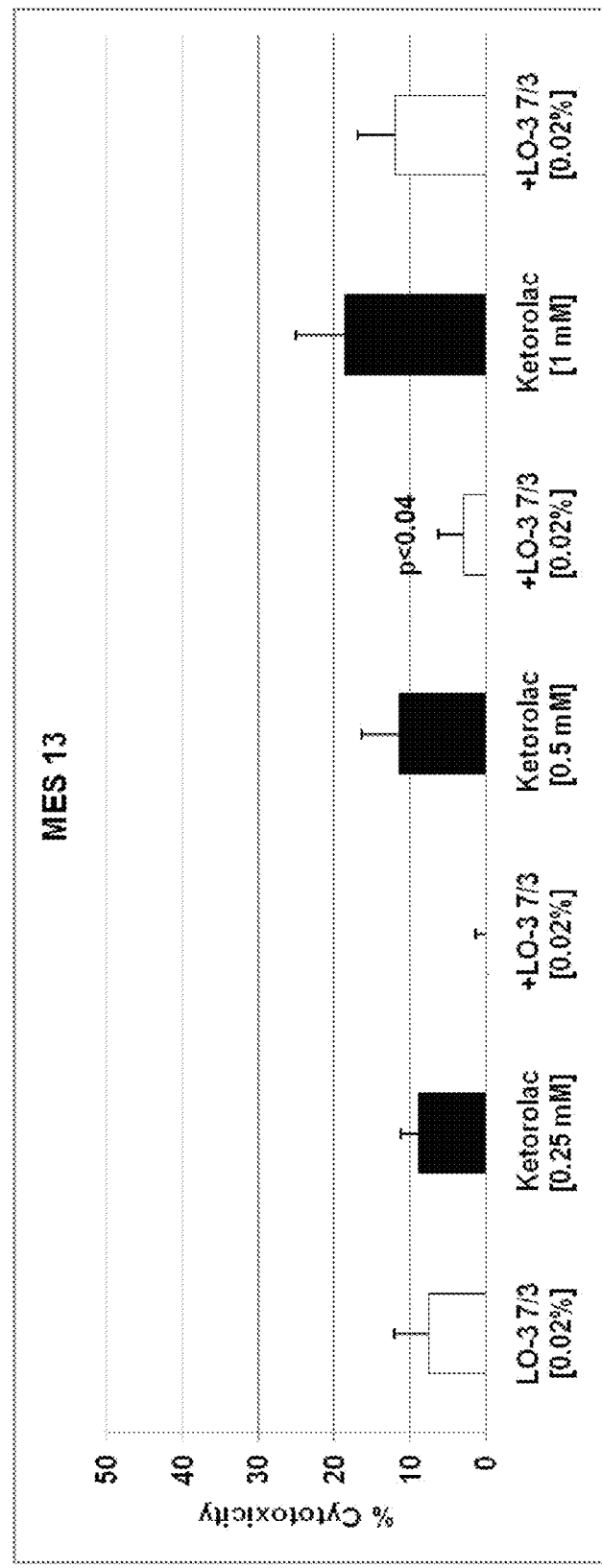
Figure 4C:
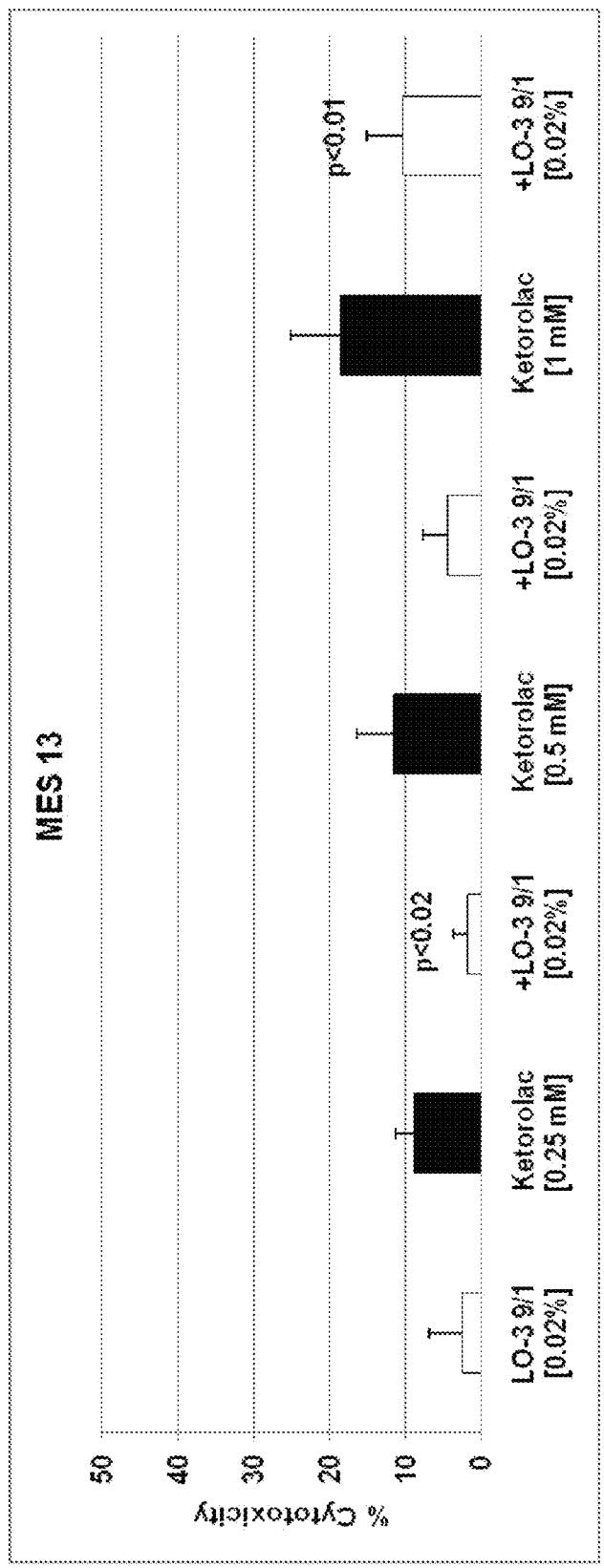
Figure 4D:
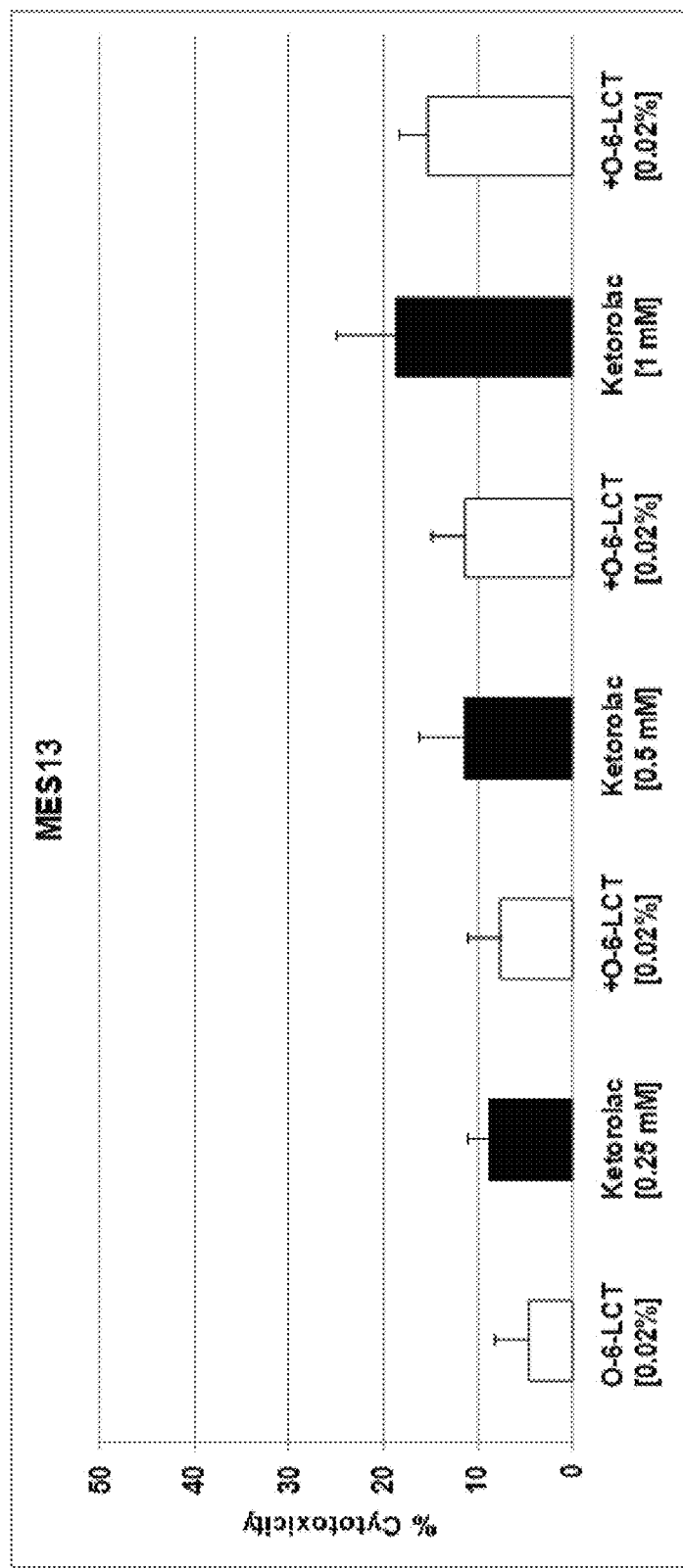

FIGS. 3A to 3C show the effects of 48 h treatment with 0.01 concentration of LO-3 5/5 (FIG. 3A), LO-3 7/3 (FIG. 3B) and LO-3 9/1 (FIG. 3C) on cytotoxic effect of Ketorolac in mouse intraglomerular mesangial cells (SV40 MES 13). Values [in % cytotoxicity of cells without treatment (=control, =0% cytotoxicity)] are given as mean±SEM; p, significance vs. Ketorolac treatment; n=4 independent experiments, using 4-6 wells per treatment and experiment.

FIG. 4A to 4D show the effects of 48 h treatment with 0.02 concentration of LO-3 5/5 (FIG. 4A), LO-3 7/3 (FIG. 4B), LO-3 9/1 (FIG. 4C) and O-6-LCT (FIG. 4D; comparative) on cytotoxic effect of Ketorolac in mouse intraglomerular mesangial cells (SV40 MES 13). Values [in cytotoxicity of cells without treatment (=control, =0% cytotoxicity)] are given as mean±SEM; p, significance vs. Ketorolac treatment; n=4 independent experiments, using 4-6 wells per treatment and experiment.

Figure 5:
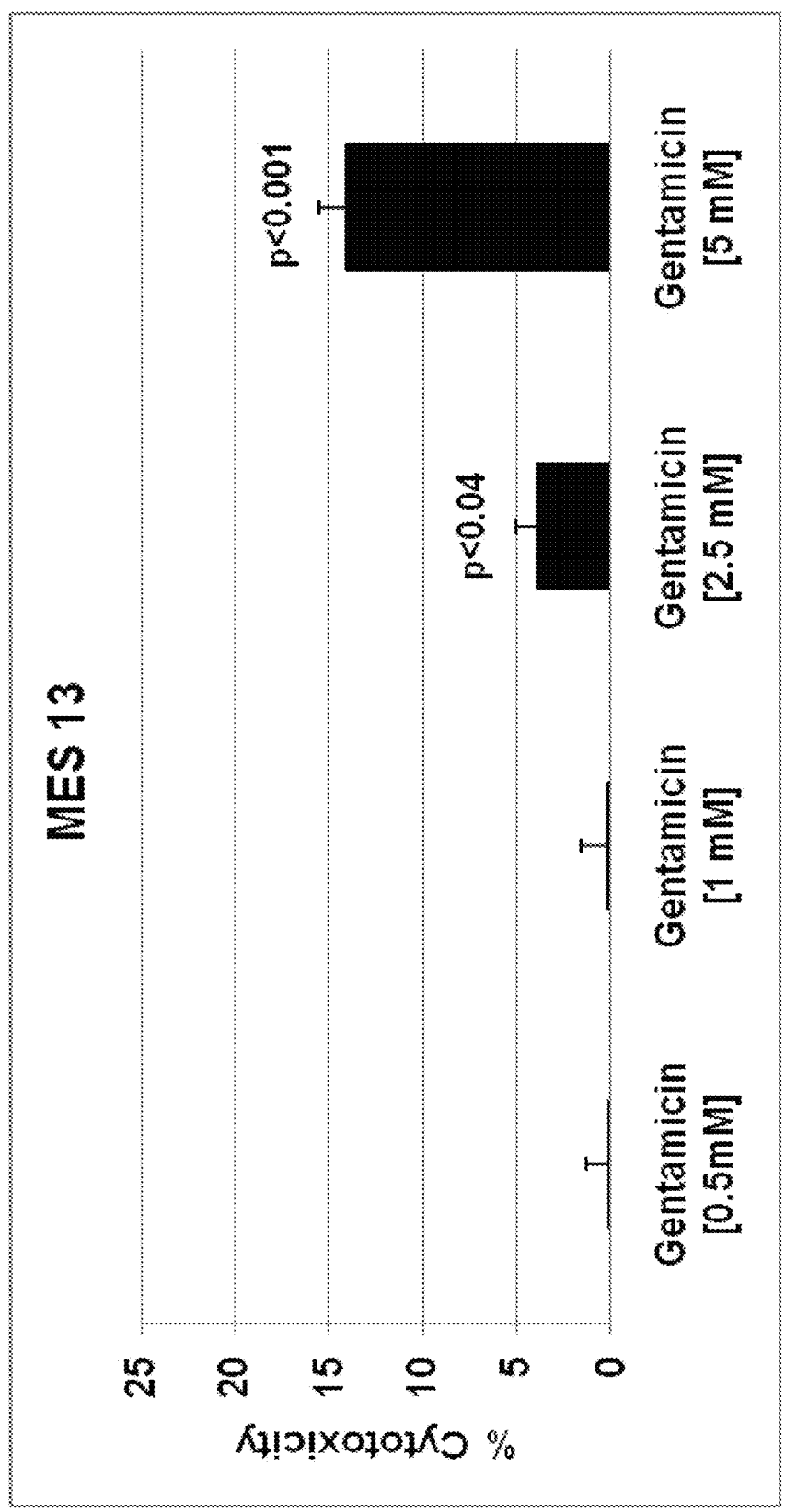
FIG. 5 shows the cytotoxic effects of 24 h treatment with Gentamicin at various concentrations on mouse intraglomerular mesangial cells (SV40 MES 13), according to an exemplary aspect.

FIG. 5 demonstrates the cytotoxic effects of 24 h treatment with Gentamicin at various concentrations on mouse intraglomerular mesangial cells (SV40 MES 13). Values [in % cytotoxicity of cells without treatment (=control, =0% cytotoxicity)] are given as mean±SEM; p, significance vs. cells without treatment (=control).

FIG. 6 shows the effects of 48 h treatment with 0.005% concentration of LO-3 9/1 on cytotoxic effect of Gentamicin in mouse intraglomerular mesangial cells (SV40 MES 13). Values [in % cytotoxicity of cells without treatment (=control, =0% cytotoxicity)] are given as mean±SEM; p, significance vs. Gentamicin treatment; n=4 independent experiments, using 4-6 wells per treatment and experiment.

While various embodiments are described herein, it will be appreciated that variations, modifications and other changes in form and detail may be made without departing from the spirit and scope of the disclosure. Such variations and modifications are to be considered within the purview and scope of the disclosure as defined by the appended claims.

REFERENCE LIST

[1] http://www.invitrogen.com/site/us/en/home/brands/Molecular-Probes/Key-Molecular-Probes-Products/Presto-Blue-Cell-Viability-Reagent.html
[2] Mansour N R, Bickle Q D (2010). Comparison of Microscopy and Alamar Blue Reduction in a Larval Based Assay for Schistosome Drug Screening. PloS Negl Trop Dis., 4(8):e795. doi:10.1371/journal.pntd.0000795.
[3] Nociari M M, Shalev A, Benias P, Russo C. (1998). A novel one-step, highly sensitive fluorometric assay to evaluate cell-mediated cytotoxicity. J Immunol Meth., 213:157-167.
[4] Hamid R, Rotshteyn Y, Rabadi L, Parikh R, Bullock P. (2004). Comparison of alamarBlue and MTT assays for high through-put screening. Toxicol In Vitro, 18:703-10.
[5] Van der Harst M R, Bull S, Laffont C M, Klein W R. (2005). Gentamicin neprotoxicyty-a comparison of in vitro finding with in vivo experiments in equines. Vet Res Commun., 29(3):247-61.
[6] Al-Nasiry S, Geusens N, Hanssens M, Luyten C, Pijnenborg R. (2007). The use of Alamar Blue assay for quantitative analysis of viability, migration and invasion of choriocarcinoma cells. Human Reproduction, 22(5):1304-1309.
[7] Sykes M L, Avery V M. (2009). Development of an Alamar Blue viability assay in 384-well format for high throughput whole cell screening of Trypanosoma brucei brucei bloodstream form strain 427. Am J Trop Med Hyg. 81(4):665-74.
[8] Heller A R et al. Omega-3 fatty acids improve the diagnosis-related outcome. Crit. Care Med 2006; 34:972-79.
[9] Elzing a et al. Modification of experimental nephrotoxicity with fish oil as the vehicle for cyclosporine. Transplantation 1987; 43:271-74.
[10] Casarett and Doull's Toxicology. The Basic Science of Poisons. McGraw-Hill, NY, 1996.
[11] Julien C et al. Postmortem brain fatty acid profile of levodopa-treated Parkinson disease patients and parkinsonian monkeys. Neurochem Int 2006; 48:404-14.
[12] Germain E et al. Anthracycline-induced cardiac toxicity is not increased by dietary omega-3 fatty acids. Pharmacol Res 2003; 47:111-17.
[13] Futamura Y. Toxicity of amiodarone on mouse pulmonary endothelial cells cultured with or without alveolar macrophages. J Toxicol Sci 1996; 21:253-67.
[14] González-Périz A et al. Docosahexaenoic acid (DHA) blunts liver injury by conversion to protective lipid mediators: protectin D1 and 17S-hydroxy DHA. FASEB J 2006; 20:2537-39.
[15] Priyamvada S et al. Studies on the protective effect of dietary fish oil on gentamicin-induced nephrotoxicity and oxidative damage in rat kidney. Prostaglandins Leukotr Essent Fatty Acids 2008; 78:369-81.
[16] Yang W et al. Attenuation of ciclosporine-induced nephrotoxicity by dietary supplementation of seal oil in Sprague-Dawley rats. J Pharm Pharmacol 2005; 57:1485-92.
[17] Wichamnn M W et al. Evaluation of clinical safety and beneficial effects of a fish oil-containing (lipoplus, MLF 541): data from a prospective, randomized multicenter trial. Crit. Care Med 2007; 35:700-6.
[18] Matta J A et al. TRPV1 is a novel target for omega-3 polyunsaturated fatty acids. J Physiol 2007; 578:397-411.
[19] Abulrob A N et al. The effect of fatty acids and analogues upon intracellular levels of doxorubicin in cells displaying P-glycoprotein mediated multidrug resistance. J Drug Target 2000; 8:247-56.
[20] Rudra P K et al. Cell-specific enhancement of doxorubicin toxicity in human tumour cells by docosahexaenoic acid. Anticancer Res 2001; 21:29-38.
[21] Ding W Q et al. Differential sensitivity of cancer cells to docosahexaenoic acid-induced cytotoxicity: the potential importance of down-regulation of superoxide dismutase 1 expression. Mol Cancer Ther 2004; 3:1109-17.
[22] Calviello G et al. docosahexaenoic acid enhances the susceptibility of human colorectal cancer cells to 5-fluorouracil. Cancer Chemother Pharmacol 2005; 55:12-20.
[23] Mahéo K et al. Differntial sensitization of cancer cells to doxorubicin by DHA: a role for lipoperoxidation. Free Radic Biol Med 2005; 15:742-51.
[24] Menendez J A et al. Endogenous supplementation with omega-3 polyunsaturated fatty acid (DHA: 22:6n3) synergistically enhances taxane cytotoxicity and downregulates Her-2/neu (c-erbB-2) oncogene expression in human breast cancer cells. Eur J Cancer Prey 2005; 14:263-70.
[25] Colas S et al. Sensitization by dietary docosahexaenoci acid of rat mammary carcinoma to anthracycline: a role for tumor vascularization. Clin Cancer Res 2006; 12:5879.86.
[26] Wang Y et al. Synthesis and preliminary antitumor activity evaluation of a DHA and doxorubicin conjugate. Bioorg Med Chem Lett 2006; 16:2974-47.
[27] Manni A et al. The impact of fish oil on the chemopreventive efficacy of tamoxifen against development of N-methyl-N-nitrosourea-induced rat mammary carcinogenesis. Cancer Prey Res 2010; 3:322-30.
[28] Harries M et al. Phase I/II study of DHA-paclitaxel in combination with carboplatin in patients with advanced malignant solid tumors. Br J Cancer 2004; 91:1651-55.
[29] Bougnoux P et al. Improving outcome of chemotherapy of metastatic breast cancer by docosahexaenoic acid: a phase II trial. Br J Cancer 2009; 101:1978-85.
[30] Fracasso P M et al. Phase 1 and pharmacokinetic study of weekly docosahexaenoic acid-paclitaxel, Taxoprexin, in resistant solid tumors. Cancer Chemother Pharmacol 2009; 63:451-58.
[31] Calder P C. Fatty acids and inflammation—From the membrane to the nucleus and from the laboratory bench to the clinic. Clin Nutr 2010; 29:5-12.
[32] Driscoll et al. Pharmacopeial compliance of fish oil-containing parenteral lipid emulsion mixtures: Globule size distribution (GSD) and fatty acid analyses. Int J Pharm 2009; 379:125-30.
[33] Frieseckes S et al. Fish oil supplementation in the parenteral nutrition of critically ill medical patients: a randomized controlled trial. Int Care Med 2008; 34:1411-20.

The invention claimed is:
1. A pharmaceutical composition for parenteral administration comprising at least one omega-3 fatty acid, medium chain triglycerides (MCT), and at least one drug,
wherein the composition is in the form of an oil-in-water emulsion, wherein the emulsion comprises 10 to 69 wt.-% MCT, based on the total amount of the oil component in the emulsion.

2. A pharmaceutical composition for parenteral administration comprising
   a) an omega-3-fatty acid component selected from the group consisting of omega-3-fatty acid triglycerides, omega-3-fatty acid ester, and a combination thereof;
   b) medium chain triglycerides (MCI); and
   c) at least one drug,
   wherein the composition is in the form of an oil-in-water emulsion,
   wherein the emulsion comprises 10 to 69 wt.-% MCT, based on the total amount of the oil component in the emulsion.

3. The pharmaceutical composition according to claim 1 wherein the at least one omega-3 fatty acid and the at least one drug are administered simultaneously.

4. The pharmaceutical composition according to claim 1 comprising
   a) an omega-3-fatty acid component selected from the group consisting of omega-3-fatty acid triglycerides, omega-3-fatty acid ethyl ester and a combination thereof; and
   b) at least one drug for use in the treatment or prophylaxis of toxic side effects of said drug.

5. The pharmaceutical composition according to claim 1 for use in mitigating toxicity effects of said drug and wherein the toxicity effects are selected from the group consisting of oxidative stress, inflammation, adverse immune response, ischemia and damages of vital organs.

6. The pharmaceutical composition according to claim 1 wherein the composition comprises omega-3-fatty acid triglycerides and medium chain triglycerides (MCT).

7. The pharmaceutical composition according to claim 1, wherein the emulsion comprises an oil component and a water component, the oil component comprising fish oil triglycerides in an amount of about 60% to about 90% based on the weight of the oil component; wherein the fish oil triglycerides comprise omega-3 fatty acids in an amount of at least 60%, based on the total weight of the fatty acids of the fish oil triglycerides; wherein the fish oil triglycerides comprise a total amount of EPA and DHA of at least 45%, based on the total weight of the fatty acids of the fish oil triglycerides; and, at least one medium-chain triglyceride, wherein a total amount of the at least one medium-chain triglyceride is from about 10% to about 40% based on the weight of the oil component.

8. The pharmaceutical composition according to claim 1 wherein the omega-3-fatty acid component comprises eicosapentaenoic acid in an amount of 30% or greater, docosahexaenoic acid in an amount of 30% or less, and docosapentaenoic acid in an amount of about 40% or less, based on the weight of the total omega-3 fatty acid content.

9. The pharmaceutical composition according to claim 1 for use in the treatment by daily parenteral administration of said omega-3 fatty acid in an amount of about 1 to about 300 mg/kg.

10. The pharmaceutical composition according to claim 1, wherein the at least one drug is a material that damages a vital organ when the material is not simultaneously administered with the at least one omega-3 fatty acid.

11. The pharmaceutical composition according to claim 1, wherein the at least one drug is present in an amount of about 0.005% to about 1.5%, based on the weight of the composition.

12. The pharmaceutical composition according to claim 1, for use in the treatment by daily parenteral administration of said drug in an amount of about 0.5 to about 50 mg/kg body weight.

13. The pharmaceutical composition according to claim 1 comprising an oil in water emulsion comprising omega-3-fatty acid triglycerides and medium chain triglycerides and a drug selected from the group consisting of ketorolac and gentamicin.

14. The pharmaceutical composition of claim 1 for use in mitigating the nephrotoxicity of a drug selected from the group consisting of ketorolac and gentamicin.

15. The pharmaceutical composition according to claim 1, wherein the at least one drug is selected from the group consisting of an amphotericin, quinolone, antineoplastic agent, amiodarone, loop diuretic, azathioprine, cyclosporine, tacrolimus, indomethacin, ketorolac and a combination thereof.

16. The pharmaceutical composition according to claim 1, wherein the at least one drug is selected from the group consisting of
   a) Antibiotics selected from the group consisting of aminoglycosides, amphotericin, chloramphenicol, ketoconazole, macrolides, quinolones and tetracyclines,
   b) Antineoplastic Agents selected from the group consisting of alkylating agents, antimetabolites, and antimitotics platinum coordination complexes,
   c) Anti-Parkinson Agents selected from the group consisting of levodopa, pramipexole, ropinirole, rotigotine and bromocriptine,
   d) Cardiovascular Agents selected from the group consisting of adenosine, amiodarone, angiotensin converting enzyme (ACE) inhibitors and flecainide,
   e) Diuretics selected from the group consisting of loop diuretics, potassium-sparing diuretics and thiazides,
   f) Immunosuppressive Agents selected from the group consisting of Azathioprine, cyclosporine, Mycophenolate and Tacrolimus,
   g) Psychotropics selected from the group consisting of haloperidol, monoamine oxidase inhibitors, phenothiazines, serotonin reuptake inhibitors and thioxanthines,
   h) Non-Steroidal Anti-Inflammatory Drugs (NSAIDs) selected from the group consisting of acetaminophen, aspirin, ibuprofen, indomethacin and ketorolac; and
   i) Pharmaceutical acceptable salts and derivatives of the drugs a) to h).

17. The pharmaceutical composition according to claim 1, wherein the at least one drug is a Non-Steroidal Anti-Inflammatory Drug selected from the group consisting of acetaminophen, aspirin, ibuprofen, indomethacin, ketorolac, and pharmaceutical acceptable salts and derivatives thereof for use in the treatment or prophylaxis of pain or swelling or redness or fever or inflammation.

18. The pharmaceutical composition according to claim 17, wherein the at least one drug is ketorolac or a pharmaceutical acceptable salt of ketorolac, for use in the treatment or prophylaxis of pain or swelling or redness or inflammation.

19. The pharmaceutical composition according to claim 18 for use in the treatment by daily parenteral administration of ketorolac tromethamine in a single dose of more than 60 mg.

20. The pharmaceutical composition according to claim 2, wherein the omega-3-fatty acid component includes an omega-3 fatty acid ethyl ester.

21. The pharmaceutical composition according to claim 18, wherein the at least one drug is ketorolac tromethamine.

22. The pharmaceutical composition according to claim 1, wherein the at least one drug is present in both the oil component and the aqueous component of the emulsion.

23. The pharmaceutical composition according to claim 2, wherein the at least one drug is present in both the oil component and the aqueous component of the emulsion.

24. The pharmaceutical composition according to claim 1, wherein the oil component of the emulsion consists of fish oil triglycerides and MCT, wherein the fish oil triglycerides include omega-3 fatty acids in an amount of at least 60%, based on the total weight of the fatty acids of the fish oil triglycerides, and wherein the fish oil triglycerides include a total amount of EPA and DHA of at least 45%, based on the total weight of the fatty acids of the fish oil triglycerides.

25. The pharmaceutical composition according to claim 2, wherein the oil component of the emulsion consists of fish oil triglycerides and MCT, wherein the fish oil triglycerides include omega-3 fatty acids in an amount of at least 60%, based on the total weight of the fatty acids of the fish oil triglycerides, and wherein the fish oil triglycerides include a total amount of EPA and DHA of at least 45%, based on the total weight of the fatty acids of the fish oil triglycerides.

26. A method of administering a drug within a pharmaceutical composition to a person in need thereof, comprising parenterally administering an effective amount of the pharmaceutical composition of claim 1 to said person.

27. The method according to claim 26, wherein the at least one omega-3 fatty acid is obtained from a marine oil, and wherein the at least one omega-3 fatty acid is in a naturally occurring form.

28. The method according to claim 26, wherein the at least one omega-3 fatty acid is obtained from a marine oil, and wherein the at least one omega-3 fatty acid is in a non-naturally occurring form.

29. The method according to claim 26, wherein the at least one omega-3 fatty acid is obtained from a marine oil, and wherein the at least one omega-3 fatty acid is attached to neutral triglycerides, ethanol as ethyl esters or a combination thereof.

30. The method according to claim 26, wherein the at least one omega-3 fatty acid comprises eicosapentaenoic acid, docosahexaenoic acid and docosapentaenoic acid.

31. The method according to claim 30, wherein the eicosapentaenoic acid is present in an amount of 30% or greater, the docosahexaenoic acid is present in an amount of 30% or less, and the docosapentaenoic acid is present in an amount of about 40% or less, based on the weight of the total omega-3 fatty acid content.

32. The method according to claim 30, wherein a total daily dosage of the at least one omega-3 fatty acid is about 1 to about 300 mg/kg, based on the weight of the total omega-3 fatty acid content.

33. The method according to claim 26, wherein the composition is in the form of an emulsion comprising an oil phase and a water phase, wherein the at least one omega-3 fatty acid is present in the oil phase and the at least one drug is present in the oil and/or water phase(s).

34. The method according to claim 26, wherein the method does not include a pretreatment process of pretreating the person with an omega-3 fatty acid source prior to parenterally administering the composition.

35. The method according to claim 26, wherein the at least one drug is a material that damages a vital organ when the material is not simultaneously administered with the at least one omega-3 fatty acid.

36. The method according to claim 26, wherein the at least one drug is selected from the group consisting of an amphotericin, quinolone, antineoplastic agent, amiodarone, loop diuretic, azathioprine, cyclosporine, tacrolimus, indomethacin, ketorolac and a combination thereof.

37. The method according to claim 26, wherein the at least one omega-3 fatty acid is present in an amount that is effective to reduce or eliminate at least one adverse drug effect selected from the group consisting of oxidative stress, inflammation, immune stimulation, ischemia of at least one vital organ, and a combination thereof.

38. The method according to claim 26, wherein the at least one drug is present in an amount of about 0.005% to about 1.5%, based on the weight of the composition.

39. The method according to claim 26, wherein a dosage of the drug is in an amount of about 0.5 to about 50 mg/kg, based on the weight of the composition.

40. The method according to claim 26, wherein the parenteral administration comprises intravenous administration.

* * * * *